(12) United States Patent
Holladay et al.

(10) Patent No.: US 8,535,728 B2
(45) Date of Patent: *Sep. 17, 2013

(54) COLLOIDAL SILVER COMPOSITION HAVING ANTIMICROBIAL PROPERTIES

(75) Inventors: Robert J. Holladay, Saratoga Springs, UT (US); Herbert Christensen, Alpine, UT (US); William Moeller, Alpine, UT (US)

(73) Assignee: American Silver, LLC, Alpine, UT (US)

( * ) Notice: Subject to any disclaimer, the term of this patent is extended or adjusted under 35 U.S.C. 154(b) by 1088 days.

This patent is subject to a terminal disclaimer.

(21) Appl. No.: 10/563,688

(22) PCT Filed: Jun. 3, 2004

(86) PCT No.: PCT/US2004/017567
§ 371 (c)(1),
(2), (4) Date: Jan. 3, 2006

(87) PCT Pub. No.: WO2005/000324
PCT Pub. Date: Jan. 6, 2005

(65) Prior Publication Data
US 2006/0182813 A1 Aug. 17, 2006

Related U.S. Application Data

(63) Continuation-in-part of application No. 09/946,834, filed on Sep. 4, 2001, now Pat. No. 6,743,348, which is a continuation of application No. 09/323,310, filed on Jun. 1, 1999, now Pat. No. 6,214,299.

(60) Provisional application No. 60/475,657, filed on Jun. 3, 2003.

(51) Int. Cl.
*A61K 33/38* (2006.01)
*A61K 9/14* (2006.01)
*A01N 59/16* (2006.01)

(52) U.S. Cl.
USPC ............................ 424/618; 424/484; 424/487

(58) Field of Classification Search
USPC .......................................... 424/618, 484, 487
See application file for complete search history.

(56) References Cited

U.S. PATENT DOCUMENTS

| | | | | |
|---|---|---|---|---|
| 2,653,893 | A | 9/1953 | Romans | 167/14 |
| 3,615,789 | A | 10/1971 | Schaller | 106/135 |
| 3,655,412 | A | 4/1972 | Kumai et al. | 106/1 |
| 4,043,932 | A | 8/1977 | Fresenius et al. | 252/95 |
| 4,201,635 | A | 5/1980 | Muller | 205/339 |
| 4,646,730 | A * | 3/1987 | Schonfeld et al. | 604/304 |
| 4,983,385 | A * | 1/1991 | Hasegawa et al. | 514/772.4 |
| 5,017,295 | A | 5/1991 | Antelman | 210/764 |
| 5,073,382 | A | 12/1991 | Antelman | 424/604 |
| 5,078,902 | A | 1/1992 | Antelman | 210/764 |
| 5,266,534 | A | 11/1993 | Atsumi et al. | 501/1 |
| 5,342,528 | A | 8/1994 | Adachi et al. | 210/668 |
| 5,516,519 | A | 5/1996 | Oka et al. | 424/105 |
| 5,785,972 | A | 7/1998 | Tyler | 424/195.1 |
| 6,027,469 | A | 2/2000 | Johnson | 604/4 |
| 6,187,293 | B1 * | 2/2001 | Ballard | 424/49 |
| 6,214,299 | B1 | 4/2001 | Holladay et al. | 422/186.21 |
| 6,743,348 | B2 | 6/2004 | Holladay et al. | 205/341 |
| 2002/0051823 | A1 * | 5/2002 | Yan et al. | 424/618 |
| 2002/0122832 | A1 | 9/2002 | Hanke et al. | 424/618 |
| 2003/0054046 | A1 | 3/2003 | Burrell et al. | 424/618 |
| 2003/0108612 | A1 | 6/2003 | Xu et al. | 424/489 |

FOREIGN PATENT DOCUMENTS

| | | |
|---|---|---|
| CN | 1379146 | 11/2002 |
| CN | 1383812 | 12/2002 |
| EP | 0136768 | 4/1985 |
| WO | WO2004083352 | 9/2004 |

OTHER PUBLICATIONS

Ultra Professional Instructions for Making Premium 'AC' Colloidal Silver with Your HVA 'Ultra Professional' System, 1999.

* cited by examiner

*Primary Examiner* — Abigail Fisher
(74) *Attorney, Agent, or Firm* — Venable LLP

(57) ABSTRACT

Colorless composition comprising silver particles and water, wherein said particles comprise an interior of elemental silver and an exterior of ionic silver oxide, wherein the silver particles are present in the water at a level of about 5-40 ppm, and wherein the composition manifests significant antimicrobial properties. Methods of use of the composition are described. The composition can be incorporated into a hydrogel with essentially no loss of antimicrobial properties.

12 Claims, No Drawings

COLLOIDAL SILVER COMPOSITION HAVING ANTIMICROBIAL PROPERTIES

The present application is a continuation-in-part of application Ser. No. 09/946,834, filed Sep. 4, 2001, which is a continuation of application Ser. No. 09/323,310, filed Jun. 1, 1999, now U.S. Pat. No. 6,214,299. To the extent permitted these applications are incorporated herein by reference. The present application claims priority to provisional application 60/475,657, filed Jun. 3, 2003, and incorporated by reference herein.

AREA OF THE ART

The present invention generally relates to colloidal silver, and more particularly to a composition of colloidal silver and a method for using said composition as an agent against organisms harmful to the health of humans.

DESCRIPTION OF THE PRIOR ART

It is well known that certain preparations of silver have germicidal properties. Silver was employed as a germicide and an antibiotic before modern antibiotics were developed. In previous centuries, users would shave silver particles into their drinking water, or submerge whole silver pieces in the drinking water, for the purpose of ingesting the silver by drinking the water. It seems likely that the practice of eating with silver utensils (i.e., silverware) resulted from a belief in the healthful properties of silver.

There may be many reasons why administering silver suspended in solution would enhance an individual's health. It is possible that such a solution operates to inhibit the growth of bacteria, viruses, and other unwanted organisms, as well as eradicating such existing bacteria, viruses, and other organisms. It is also possible that a solution of silver can have an anti-inflammatory effect, sufficient to reduce symptoms of asthma.

The present invention describes the use of a silver composition in water to treat certain human ailments. An embodiment of the invention is a silver composition comprising small particles of silver which comprise an interior of metallic silver and an exterior of ionic silver which particles are suspended in water. A preferred embodiment of the invention is a silver composition comprising particles of silver wherein more than 50% of the number of particles are less than 0.015 micrometers in size and the particles are colloidally suspended in water.

SUMMARY OF THE INVENTION

The present invention is generally directed to the use of silver, at a level of 5 to 40 ppm in water, to kill or to disable microorganisms which are hazardous to human beings. The present invention specifically is directed to compositions comprising silver particles, said particles comprising an interior of elemental silver and an exterior of ionic silver oxide, and water, wherein the silver particles are placed in colloidal suspension in the water at a level of 5-40 ppm total silver. An embodiment of the present invention comprises silver particles in water, at a concentration of 5-40 ppm, wherein more than 50% of the silver particles have a maximum dimension less than 0.015 micrometers. The composition of silver in water of this invention is an effective antimicrobial agent. This invention is directed to silver compositions, of 5-40 ppm silver in water, which are effective antimicrobial agents, and to methods of using said silver compositions as antimicrobial agents.

A preferred embodiment of the present invention is directed to compositions of silver in water made using a modification of the device and methods described in U.S. Pat. No. 6,214,299, which is a parent of the instant application and is incorporated herein by reference.

The device and process of U.S. Pat. No. 6,214,299 have been modified and improved to provide the silver composition of the present invention. Essentially, the eight-silver/one common electrode device as disclosed in the patent has been modified and scaled to fit a 75-gallon water chamber. To start the process approximately 70 gallons of high purity water are placed in the chamber. To this is added approximately five gallons of silver composition produced in a prior production run. This is necessary because the high purity water is insufficiently conductive for the process to occur properly. The water chamber is equipped with an air input that allows a stream of air bubbles to be streamed through the liquid during the processing. It has been discovered that this approach gives improved mixing as compared to the impeller mixer described in the patent.

The electrode device is operated at approximately ten thousand volts alternating current (with each silver electrode having an individual voltage supply) as described in the patent. It has been found that voltages significantly lower than this produce a composition with larger particles not having the optimal properties described herein. Voltages significantly higher tend to produce a solution with significant ionic silver dissolved therein. The present composition comprises in excess of 97% metallic silver with essentially no free ionic silver in solution.

The silver concentration is determined according to the methods explained below. Essentially, the device is operated continuously and samples are analyzed until the desired silver concentration is attained. The 10 ppm composition requires approximately one and one half days of operation. The 22 ppm solution requires approximately three days, and the 32 ppm composition requires approximately six days. The rate of the process appears to slow as the higher concentrations are attained. Higher concentrations take a prohibitively long time with the ultimate highest concentration being about 50 ppm, at least within the current parameters.

The compositions all have the size characteristics described below and unlike conventional silver compositions are completely colorless and stable to light and temperature changes without use of any additives. The compositions are unreactive towards added hydrogen peroxide.

Hydrogen peroxide, a know disinfecting agent, has been found to have a synergistic interaction with the inventive silver composition. Hydrogen peroxide is available in concentration of 30% wght/v (% weight per volume or weight percent) or higher. Although the higher concentrations are usable, the preferred concentrations are in the range of 1 to 5% wght/v.

A preferred embodiment of the present invention is directed to compositions comprising 5 to 40 ppm silver, said silver being primarily elemental silver, 1 to 3 wght % hydrogen peroxide, and water. A preferred embodiment of the present invention is the use, and method of use, of compositions comprising 10 to 40 ppm silver and 1 to 3 wght % hydrogen peroxide in water as antimicrobial agents.

Although a large number of tests employing the colloidal silver solution alone are presented below, it is also demonstrated that certain vehicles can significantly improve the results obtainable with the silver. Specifically it has been found that formulating the aqueous silver colloid as a semi-solid hydrogel significantly enhances it efficacy. Hydrogels are hydrophilic gels produced by adding certain hydrophilic organic polymers to an aqueous solution—in this case a solution containing the inventive colloidal silver solution. As would be expected, the hydrogel improves the retention of the silver on a surface such as a wound. For wound care a hydrogel also has the significant advantage of protecting the tissues surrounding the wound and preventing desiccation, which factors enhance wound healing. Most significantly, the hydrogel does not interfere with the antimicrobial properties of the colloidal silver nor does it appear to significantly slow the diffusion of the active silver colloids.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved colloidal silver product with significant abilities to kill human pathogens both in vivo and in vitro.

Generally, the present invention represents a novel approach to killing or disabling microorganisms which are hazardous to human beings by the use of silver particles in water, at a concentration of 5 to 40 ppm silver. Depending upon the application, the silver composition may be used internally or externally. Depending on the application, the silver composition may also contain hydrogen peroxide.

Preferred Embodiments

Non-limiting preferred embodiments are presented in the following:

A composition comprising silver particles, colloidally suspended in water, wherein the total content of silver is between 5 and 40 ppm, which composition kills or disables microorganisms which are hazardous to the human body.

A composition comprising silver particles, colloidally suspended in water, wherein the total content of silver is about 10±2 ppm, which composition kills or disables microorganisms which are hazardous to the human body.

A composition comprising silver particles, colloidally suspended in water, wherein the total content of silver is about 22±2 ppm, which composition kills or disables microorganisms which are hazardous to the human body.

A composition comprising silver particles, colloidally suspended in water, wherein the total content of silver is about 32±3 ppm, which composition kills or disables microorganisms which are hazardous to the human body.

It will be appreciated that specifying the total amount of silver in a composition of particles does not completely specify the material. As the particles comprising the composition are made smaller, a given concentration of silver will represent a larger number of particles. In addition, the total surface area for a given silver concentration will increase. Therefore, particles size and range of particle size is an important parameter for defining an effective inventive composition.

A further class of embodiments is any of the above-described compositions, wherein more than 50% of the silver particles have a maximum dimension less than 0.015 micrometers.

A further class of embodiments is any of the above-described compositions, wherein more than 75% of the silver particles have a maximum dimension less than 0.015 micrometers.

A further class of embodiments is any of the above-described compositions, wherein more than 90% of the silver particles have a maximum dimension less than 0.02 micrometers.

A further class of embodiments is any of the above-described compositions, wherein more than 75% of the silver particles have a minimum dimension greater than 0.005 micrometers.

A further class of embodiments is any of the above-described compositions, wherein more than 90% of the silver particles have a minimum dimension greater than 0.005 micrometers.

A further class of embodiments is any of the above-described compositions, wherein the silver particles comprise both silver in the zero-valent, that is, metallic, oxidation state [Ag(0)] and a coating of silver in an ionic oxidation selected from the group consisting of Ag(I), Ag(II), and Ag(III).

A further class of embodiments is any of the above-described compositions, wherein the silver particles comprise both silver in the zero-valent, that is metallic, oxidation state [Ag(0)] and a coating of silver oxide with the stoichiometry AgO.

Experimental evidence shows that AgO in the particles of the present invention is at least partially in the form of $Ag_4O_4$—that is, silver II oxide. In a molecule of this material two of the silver atoms are in the $1^+$ state (silver I) while the other two silver molecules are in the $3^+$ state (silver III). Under certain conditions these molecules can give rise to silver atoms in the $2^+$ (silver II) state.

A further class of embodiments is the combination of any of the above-described embodiments with hydrogen peroxide, at a level of 1-3 wgt % hydrogen peroxide in the final product.

EXAMPLES

Formation of Composition

Compositions of silver in water can be made according to procedures set forth in U.S. Pat. No. 6,214,299, incorporated by reference herewith.

A preferred method for producing a composition comprising silver according to this invention utilizes a electrochemical cell comprising electrodes and comprises the steps (a) placing a silver electrode in contact with a quantity of high purity water;

(b) conveying electrical current through the silver electrode to thereby separate particles of silver from said silver electrode in a manner sufficient to cause production of suspended silver particles within the water; and (c) agitating the water during said production of suspended silver particles to thereby disperse the silver particles into a more uniform concentration within said water such that a higher quantity of suspended silver particles can be produced per batch.

Another preferred method for producing a composition comprising silver utilizes an electrochemical cell and comprises the steps of:

(a) establishing an electrical circuit comprising a current source, and a first conductor electrically connected to said current source and a second conductor electrically connected to said current source, wherein said first conductor is disposed spaced apart from said second conductor, and wherein at least one of the conductors is made of elemental silver;

(b) closing the circuit by placing the first conductor and the second conductor in communication with a fluidic resistor;

(c) operating the current source to supply alternating current simultaneously to the first conductor and the second conductor such that voltage is increasing and decreasing within the first and second conductors in alternating tandem to thereby cause silver particles to separate from the first electrode and enter the fluidic resistor and become disposed in suspension within said fluidic resistor; and (d) selectively adjusting the electrodes by moving them toward the fluidic resistor to compensate for decrease in electrode length due to gradual separation of silver particles therefrom to thereby prevent arcing from occurring between the electrodes and said fluidic resistor.

The analysis of the silver content in the silver compositions of this invention may be done by atomic absorption (AA), inductively coupled plasma/atomic emission (ICP/AES), or other techniques known to one of ordinary skill in the art to be sensitive to silver in the appropriate concentration range. If the particles of the silver composition are small and uniformly sized (for example, 0.01 micrometers or less), a reasonably accurate assay may be obtained by running the colloid directly by AA or ICP/AES. This is because the sample preparation for AA ionizes essentially all of the silver allowing its ready detection.

If the compositions comprise particles as large as 0.2 micrometers, it is preferred to use a digestion procedure. The digestion procedure is not necessarily ideal for silver compositions that may have been manufactured or stored in contact with halides or other anionic species that may react with finely divided silver, or combined with protein or other gelatinous material. An embodiment of the digestion procedure is as follows:

1 Take a 10 ml aliquot of a thoroughly mixed or shaken silver composition to be analyzed, and place it in a clean polycarbonate bottle or other container of suitable material (generally, the bottle) with a tight fitting lid. A size of 30-100 ml is preferred.

2 With a micropipette or dropper, add 0.1 ml of nitric acid, reagent grade to the silver composition in the bottle.

3 With the lid of the bottle tightly in place, heat the silver composition to 80° C. with mild agitation for a time sufficient to dissolve the silver—dissolution is essentially instantaneous.

4 Allow the resulting mixture to cool to room temperature with the lid in place. Shake the bottle thoroughly.

5 Utilize AA, ICP/AES, or equivalent means to analyze the silver content of the silver mixture. Preferably, one will utilize a freshly prepared standard or standards, preferably prepared according the equipment manufacturer's instructions, with appropriate dilution as needed.

6 When reporting results, one must taken into account all dilutions during preparation, including the 1% dilution caused by addition of the nitric acid.

Analysis of Physical/Chemical Form of Silver

A. Introduction

A sample of a composition, nominally containing 22 ppm silver in water, was analyzed by time-of-flight secondary ion mass spectrometry (TOF-SIMS) in order to determine the form of silver in the composition. The conclusion is that the bulk of the silver exists as silver (0) [that is, metallic silver] and that there is a surface coating which as on average a composition of silver (II) oxide [AgO]. As mentioned above silver (II) oxide is usually a stoichiometric combination of silver (I) and silver (III).

B. Experimental Procedure

A few drops of the 22 ppm inventive silver composition were evaporated to dryness on a silicon substrate at ambient temperature. The residue was analyzed by TOF-SIMS, and is denoted as the sample. A reference silver (II) oxide (AgO) material was analyzed by placing a few particles of the reference powder as received from the vendor on a silicon substrate, and is denoted as the reference.

The Time-of-Flight Secondary Ion Mass Spectrometry technique (TOF-SIMS) is based on the principle of bombarding a solid sample with a pulsed, finely focused beam of primary ions, and then analyzing the secondary ions produced from the surface of the sample via a time-of-flight mass spectrograph. This analytical technique is surface sensitive, deriving its information from a layer that extends to approximately 20 to 40 Å (one Angstrom=$1\times10^{-4}$ micrometers) below the surface. The TOF-SIMS technique is normally used as a survey tool to identify the composition of unknown samples. It is capable of quantification if the appropriate microanalytical standards are available for calibration. This analysis was carried out using standard high mass-resolution conditions.

C. Results

Negative ion mass were obtained for the Ag(II)O reference material and the product sample, respectively. The mass spectral region for both spectra showed the presence of AgO—species. The data suggest that silver (II) is the average oxidation state of the silver present on the surface of the sample particles. The silver oxide (AgO) signals exhibit significantly higher intensity in the reference sample compared to the product sample which is probably because metallic silver is dominant in the sample. It will be appreciated that as the average particle size in the sample is decreased the ratio of silver to silver oxide will also decrease as more silver oxide will be present.

Size Analysis

It is likely that the unusual effectiveness of the silver preparations described herein is due to the relationship between the surface properties/inner properties (i.e., oxide/metal) of the particles and the size distribution of the particles. The smaller the average particle size, the greater the surface area and the greater the contribution of the particular surface chemistry. However, if the particles are excessively small there can be a loss of stability and/or other interactions that negatively affect the product. The silver compositions of the instant invention are remarkable because they are stable in essentially pure water without surfactants, etc. Also, the materials are essentially colorless while other colloidal silver preparations (particularly with larger particle sizes) usually show colors. These properties are a result of the exact manufacturing conditions as discussed above.

Digital analysis of the composition showed that there is an average particle diameter of 0.0106 micrometers with a range of 0.005 micrometer to 0.0851 micrometers. However, size distribution analysis shows that more than 95% of the particles were between about 0.005 micrometers and about 0.015 micrometers in diameter.

Evidence of Efficacy of 22 ppm Silver Composition Against *Bacillus Subtilis*

A. Purpose of Example

The purpose of this example is to demonstrate the antimicrobial activity of the silver-based composition of the present invention on bacterial endospores from the test organism *Bacillus subtilis*. This was accomplished by performing a standard kill-time assay using a suspension of *B. subtilis* endospores. Normally, bacterial endospores are resistant to killing.

B. Material and Methods

Test Organism.

A test suspension containing endospores from *Bacillus subtilis* (ATTC #19659) was prepared from a culture grown on nutrient agar, to which additional sporulation enhancement ingredients were added. Plates were harvested with sterile water and endospores were purified by repeated centrifugations and resuspensions in water. The final wash was in 70% ethanol for 30 min, to ensure the destruction of all vegetative bacteria. The spores were resuspended in water containing 0.1% Tween 80 (brand of polysorbate surfactant) to prevent clumping.

Neutralizer.

The Neutralizer mixture consisted of 12.7% Tween® 80 (brand of polysorbate), 6.0% Tamol® SN (brand of sodium salt of naphthalene-formaldehyde condensate), 1.7% lecithin, 1% Peptone, and 0.1% Cystine. This solution was intended to neutralize any chemicals so they would not affect subsequent growth of the bacteria.

Kill-Time Procedure:

a) A 9.9 ml aliquot of the disinfectant (inventive 22 ppm silver composition, in water) was placed in a sterile 20 mm×150 mm tube. The tube was equilibrated in a 20° C. water bath.

b) A 9.9 ml aliquot of the disinfectant (inventive 22 ppm silver composition, in water) was placed in a sterile 20 mm×150 mm tube. The tube was equilibrated in a 20° C. water bath.

c) At 30 min. 1 hr, and 4 hr, one ml of organism/disinfectant suspension was removed to a tube containing nine ml of Neutralizer. The tube was mixed thoroughly.

d) After two min, the neutralized suspension was serially diluted 1:10, in physiological saline solution (PSS).

e) The number of viable organisms in selected dilution tubes was assayed by membrane filtration. One ml aliquots were plated in duplicate. The membranes were washed with about 100 ml of sterile PSS and removed to Nutrient Agar plates. The plates were incubated at 37° C. for 20 hr.

f) The number of colonies on each filter was counted and log reductions were computed.

Controls:

a) Titers of the test suspensions were computed by performing membrane filtration assays of selected 1:10 dilutions of the test suspensions in PSS.

b) A neutralizer control was performed by inoculating a mixture of 9 ml neutralizer and 1 ml of disinfectant with 100 μl of a dilution of the titer containing 100 cfu. This produced about 10 cfu/ml in the tube, which was allowed to stand for 20 minutes prior to assay by membrane filtration using duplicate 1 ml samples.

C. Results

*Bacillus subtilis* Titer:

|  | Dilution: | | |
|---|---|---|---|
|  | $1:1 \times 10^6$ | $1:1 \times 10^7$ | $1:1 \times 10^8$ |
| Number of colonies: | TNTC | 75 | 7 |
|  | TNTC | 58 | 8 |

TNTC = too numerous to count

Dilution of *B. subtilus* Spore/Disinfectant Suspension:

| Time | $1:1 \times 10^1$ | $1:1 \times 10^2$ | $1:1 \times 10^3$ | $1:1 \times 10^4$ | $1:1 \times 10^5$ | $1:1 \times 10^6$ |
|---|---|---|---|---|---|---|
| 30 min | — | — | TNTC | TNTC | 57 | 10 |
|  | — | — | TNTC | TNTC | 51 | 7 |
| 1 hr | — | — | TNTC | TNTC | 28 | 3 |
|  | — | — | TNTC | TNTC | 55 | 3 |
| 2 hr | — | TNTC | TNTC | 126 | 23 | — |
|  | — | TNTC | TNTC | 183 | 17 | — |
| 4 hr | TNTC | TNTC | 88 | 12 | — | — |
|  | TNTC | TNTC | 69 | 12 | — | — |

TNTC = too numerous to count
Neutralization Control: $1:1 \times 10^8$

D. Discussion

Results of the titer showed a viable *B. subtilis* spore concentration of $6.65 \times 10^8$ spores per ml in the original suspension. Inoculation of 9.9 ml of disinfectant with 100 μl of this suspension produced an initial concentration of $6.65 \times 10^6$ spores per ml in the assay tube.

Results from these procedures allowed log reductions (LR) and Percent Kill (PK) values to be calculated. They are listed in the table below. Values were computed using the formulae: $LR = -\text{Log}(S/S_o)$ and $PK = (1-(S/S_o)) \times 100$; where S=concentration of organisms at a specific time; and $S_o$=the initial concentration of organisms at time zero.

| Time | LOG REDUCTION | PERCENT KILL |
|---|---|---|
| 30 min | 0.090 | 18.8 |
| 1 hr | 0.205 | 37.6 |
| 2 hr | 0.634 | 76.8 |
| 4 hr | 1.928 | 98.8 |

Neutralization control data showed that the disinfectant was adequately neutralized. Actual counts correspond to those resulting from dilution without appreciable killing.

The disinfectant preparation tested here displayed good sporicidal activity against *B. subtilis* spores. *B. subtilis* is a common species used in sporicidal testing and belongs to the same genus as the organism that causes anthrax. Because of their genetic similarities, *B. subtilis* spores have been used as a non-pathogenic surrogate for *Bacillus anthracis*, the anthrax bacterium. Therefore, these results are applicable to anthrax. It is expected that longer exposure would result in additional killing.

Evidence of Efficacy of 10 ppm Silver and 1.0% $H_2O_2$ Composition and 14 ppm Silver and 1.5% $H_2O_2$ Composition Against *Bacillus Subtilis*

A. Purpose of Example

The purpose of this example is to demonstrate the antimicrobial activity of two silver-based compositions of the present invention on bacterial endospores from the test organism *Bacillus subtilis*. This was accomplished by performing standard kill-time assays using a suspension of *B. subtilis* endospores. Viewed relative to the previous example (employing 22 ppm silver), this example establishes the promoting effect of hydrogen peroxide ($H_2O_2$) on the antimicrobial properties of silver compositions. Hydrogen peroxide is stable in the presence of the silver compositions of the present invention. While hydrogen peroxide has significant antimicrobial properties itself, it is frequently broken down by catalase or other microbial enzymes. However, the hydrogen peroxide is capable of weakening bacterial cell walls and enhancing entry of the silver particles before any enzymatic destruction of the hydrogen peroxide can occur.

B. Material and Methods

1 Test Organism.

A test suspension containing endospores from *Bacillus subtilis* (ATCC #19659) was prepared from a culture grown on Nutrient Agar, to which additional sporulation enhancers were added. Plates were harvested with sterile water and endospores were purified by repeated centrifugations and resuspensions in water. The final wash was in 70% ethanol for 30 min, to ensure the death of all vegetative bacteria. The spores were resuspended in water containing 0.1% Tween® 80 (brand of polysorbate) to prevent clumping.

2 Neutralizer.

The Neutralizer mixture consisted of 12.7% Tween 80, 6.0% Tamol® SN (brand of sodium salt of naphthalene-formaldehyde condensate), 1.7% lecithin, 1% Peptone, and 0.1% Cystine. This solution was intended to neutralize any chemicals so they would not affect subsequent growth of the bacteria.

3 Kill-time Procedure:

a) A 9.9 ml aliquot of each of the disinfectants (inventive colloidal silver compositions: one containing 14 ppm silver and 1.5% H202; the other containing 10 ppm silver and 1.0% $H_2O_2$) was placed in a sterile 20 mm×150 mm tube. The tubes were equilibrated in a 20° C. water bath.

b) Each tube of disinfectant was inoculated with 100 µl of the test organism suspension at time zero.

c) At 10 min, 30 min, 1 hr, 2 hr, 4 hr, 6 hr, and 8 hr, one ml of organism/disinfectant suspension was removed to a tube containing nine ml of neutralizer. The tube was mixed thoroughly.

d) After two min, the neutralized suspension was serially diluted 1:10, in physiological saline solution (PSS).

e) The number of viable organisms in selected dilution tubes was assayed by membrane filtration. One ml aliquots were plated in duplicate. The membranes were washed with about 100 ml of sterile PSS and removed to Columbia Agar plates. The plates were incubated at 37° C. for 20 hr.

f) The number of colonies on each filter was counted and log reductions computed.

4. Controls:

a) Titers of the test suspensions were computed by performing membrane filtration assays of selected 1:10 dilutions of the test suspensions in PSS.

b) A neutralizer control was performed by inoculating a mixture of 9 ml of neutralizer and 1 ml of disinfectant with 100 µl of the 1:$10^3$ dilution of the titer. This produced about 2,000 cfu/ml in the tube, which was allowed to stand for 20 minutes prior to diluting 1:10. Both tubes were assayed by membrane filtration using duplicate 1 ml. samples.

C. Results

Titer of *Bacillus subtilis* Spores:

|  | Dilution: | | |
| --- | --- | --- | --- |
|  | 1:1 × $10^6$ | 1:1 × $10^7$ | 1:1 × $10^8$ |
| Number of colonies: | TNTC | 36 | 5 |
|  | TNTC | 27 | 4 |

TNTC = too numerous to count.

Solution containing 14 ppm silver and 1.5% $H_2O_2$:
Dilution of *B. subtilis* Spore/Disinfectant Suspension:

| Time | 1:1 × $10^1$ | 1:1 × $10^2$ | 1:1 × $10^3$ | 1:1 × $10^4$ | 1:1 × $10^5$ |
| --- | --- | --- | --- | --- | --- |
| 10 min | — | — | TNTC | TNTC | 227 |
|  | — | — | TNTC | TNTC | 265 |
| 30 min | — | — | TNTC | TNTC | 258 |
|  | — | — | TNTC | TNTC | 273 |
| 1 hr | — | — | TNTC | TNTC | 55 |
|  | — | — | TNTC | TNTC | 33 |
| 2 hr | — | TNTC | 207 | 29 | — |
|  | — | TNTC | 237 | 24 | — |
| 4 hr | 59 | 3 | 1 | | |
|  | 57 | 5 | 1 | | |
| 6 hr | 0 | 0 | 0 | | |
|  | 3 | 0 | 0 | | |
| 8 hr | 1 | 0 | 0 | | |
|  | 1 | 0 | 0 | | |

TNTC = too numerous to count.

Neutralization Control:

| Undiluted | 1:1 × $10^1$ |
| --- | --- |
| TNTC | 195 |
| TNTC | 210 |

TNTC = too numerous to count.

Solution containing 10 ppm silver and 1.0% $H_2O_2$:
Dilution of *B. subtilis* Spore/Disinfectant Suspension:

| Time | 1:1 × $10^1$ | 1:1 × $10^2$ | 1:1 × $10^3$ | 1:1 × $10^4$ | 1:1 × $10^5$ |
| --- | --- | --- | --- | --- | --- |
| 10 min | — | — | TNTC | TNTC | 230 |
|  | — | — | TNTC | TNTC | 287 |
| 30 min | — | — | TNTC | TNTC | 254 |
|  | — | — | TNTC | TNTC | 260 |
| 1 hr | — | — | TNTC | TNTC | 146 |
|  | — | — | TNTC | TNTC | 124 |
| 2 hr | — | TNTC | TNTC | 64 | — |
|  | — | TNTC | TNTC | 71 | — |
| 4 hr | TNTC | 72 | 5 | | |
|  | TNTC | 77 | 5 | | |
| 6 hr | 0 | 0 | 0 | | |
|  | 2 | 0 | 0 | | |
| 8 hr | 0 | 0 | 0 | | |
|  | 0 | 0 | 0 | | |

TNTC = too numerous to count.

Neutralization Control:

| Undiluted | 1:1 × $10^1$ |
| --- | --- |
| TNTC | 200 |
| TNTC | 184 |

TNTC = too numerous to count.

D. Discussion

The data showed a viable *B. subtilis* spore concentration of 2.59×$10^8$ spores per ml in the original suspension. Inoculation of 9.9 ml of disinfectant with 100 µl of this suspension produced an initial concentration of 2.59×$10^5$ spores per ml in the assay tube.

Results from these procedures allowed log reductions (LR) and Percent Kill (PK) values to be calculated. They are listed in the following table. Values were computed using the formulae: LR=−Log(S/So) and PK=(1−(S/So))×100; where. S=concentration of organisms at a specific time; and So=the initial concentration of organisms at time zero. Since there was no significant kill within 30 min, the 10 min data was used for the So values. The 6 hr and 8 hr exposure times did not produce counts high enough to be reliable. Therefore, these data were not used in the linear regressions. Linear regressions were performed on the log reduction values using the 'fitted line plots' command in the Minitab statistical software package. The regression equations produced, and the times required to effect a six-log reduction are shown along with the log reduction and percent kill values in the following table.

| Time | 14 ppm SILVER + 1.5% $H_2O_2$ | | 10 ppm SILVER + 1.0% $H_2O_2$ | |
|---|---|---|---|---|
| | LOG REDUCTION | PERCENT KILL | LOG REDUCTION | PERCENT KILL |
| 30 min | −0.03 | −7.9 | 0.003 | 0.6 |
| 1 hr | 0.66 | 78.0 | 0.28 | 47.8 |
| 2 hr | 2.05 | 99.1 | 1.58 | 97.4 |
| 4 hr | 4.63 | 99.998 | 3.54 | 99.97 |

Regression Analysis

Equation for 14 ppm calculated line: Y=−0.66704+1.32936x. Equation for 10 ppm calculated line: Y=−0.59690+1.03933x. These equations predict that the time for a 6-log reduction is 5.02 hrs for the 14 ppm composition and 6.35 hrs for the 10 ppm composition.

The neutralization control data showed that the disinfectant was adequately neutralized. Expected counts corresponded to those expected from the dilution.

The experimental disinfectant solutions tested exhibited significant sporicidal activity against *B. subtilis* spores. The *B. subtilis* strain used in these evaluations is the same one specified in the AOAC sporicidal test. Spores from this organism represent a significant challenge for most disinfectants. The times required to effect a six log reduction are in line with the sporicidal label claims of many cold sterilants.

Evidence of Efficacy of 10 ppm Silver Composition as a Broad Spectrum Antimicrobial A. Methods MIC (minimum inhibitory concentration) and MBC (minimum bactericidal concentration) tests were performed according to the standard broth microdilution method. The MIC is defined as the lowest concentration of an antibiotic that will inhibit the (in vitro) growth of an infectious organism. Results are reported in micrograms per ml. For medical antibiotics the interpretation of in vitro data is based on achievable serum concentrations of the drug, which may vary depending on dose, route of administration, degree of protein binding, site of infection, age and weight of the patient, and other factors. The MBC is defined as the lowest concentration of an antimicrobial agent needed to kill 99.9% of the initial organism inoculum.

The test was preformed by growing pure cultures of each of the test organisms in liquid culture. Turbidometric measurements were used to control the concentration of the culture. Serial dilutions of each test antibiotic were made in nutrient broth. The dilutions were calculated to cover the susceptible ranges for each organism for each agent. A standard amount of the test culture was added to each tube and the tube returned to an incubator (37±2° C.) for growth. The tubes were checked turbidometrically to determine bacterial growth. Below the MIC concentration the tubes showed an increase in optical density with time indicating bacterial growth. The lowest concentration of the antibiotic that showed no growth was the MIC. The "no growth" tubes were then subcultured in fresh medium. The "no growth" tube with the lowest concentration of antibiotic that showed no growth on subculturing was the MBC.

B. Results:

| Organism | Antimicrobial (ppm) | | | | | |
|---|---|---|---|---|---|---|
| | Tetracycline | Ofloxacin | Penicillin G | Cefaperazone | Erythromycin | Silver |
| S. pyogenes | 0.625/>5 | 1.25/2.5 | >5.0 | 0.313/1.25 | 0.003/0.019 | 2.5/5.0 |
| S. mutans | 0.625/>5 | 2.5/>5.0 | 0.521/>5 | 1.25/>5 | 0.009/0.019 | 2.5/10.0 |
| S gordonii | 0.156/0.625 | 2.5/5.0 | 0.009/0.039 | 1.25/1.25 | 0.005/0.019 | 2:5/10.0 |
| S. pneumoniae | 0.078/0.625 | 2.5/2.5 | 0.019/0.019 | 0.313/0.313 | 0.002/0.004 | 2.5/2.5 |
| S. faecalis | 0.313/>5 | 1.25/5.0 | 5.0/>5.0 | >5.0 | 0.009/1.25 | 10.0/10.0 |
| S. aureus | 0.313/>5 | 0.417/0.625 | 2.5/>5.0 | 5.0/5.0 | 0.039/>5.0 | 5.0/5.0 |
| P. aeruginosa | 0.078/5 | 0.156/0.313 | 0.13/>5.0 | 2.5/5.0 | 2.5/>5.0 | 1.67/5 |
| E. coli | 1.67/>5 | 0.104/0.156 | >5.0 | 0.625/>5.0 | 5.0/>5.0 | 2.5/2.5 |
| E. aerogenes | >5 | 0.078/0.156 | >5.0 | 2.92/>5.0 | >5.0 | 2.5/2.5 |
| E. cloacae | 1.67/>5 | 0.156/0.156 | >5.0 | >5.0 | >5.0 | 2.5/5.0 |
| S. typhimurium | 1.25/>5 | 0.078/0.156 | >5.0 | 1.25/2.5 | 5.0/>5.0 | 2.5/5.0 |
| S arizona | 0.625/>5 | 0.078/0.078 | >5.0 | 0.833/>5.0 | 4.17/>5.0 | 2.5/5.0 |
| S. boydii | 1.25/>5 | 0.078/0.156 | >5.0 | 0.625/0.625 | 5.0/>5.0 | 1.25/1.25 |
| K. pneumoniae | 2.5/>5 | 0.417/0.625 | >5.0 | >5.0 | >5.0 | 2.5/2.5 |
| K. oxytoca | 1.25/>5 | 10.104/0.156 | >5.0 | 1.25/>5.0 | >5.0 | 1.25/1.25 |

Data are presented as MIC/MBC (minimum inhibitory concentration/minimum bactericidal concentration) in parts per million (ppm)); ">" denotes that the concentration needed to obtain the MIC or the MBC was higher than test parameters measured for the test. For example, the highest concentration of tetracycline used on *S. pyogene* was 5 ppm. At that concentration there was still growth upon subculturing of the "no growth" tubes. Therefore, the MBC must be >(greater than) 5 ppm.

The MIC/MBC of *E. coli* strain O 157:H7, which has been associated with outbreaks of hemorrhagic diarrhea and colitis, was determined in a subsequent study. The MIC was determined to be 2.5 ppm and the MBC was determined to be 5 ppm.

C. Conclusion

The 10 ppm silver composition of the present invention was tested and found to be both bacteriostatic and bactericidal for all organisms tested. In other studies, this composition was compared to other commercially available colloidal silver products and found to have a superior activity to all other preparations tested (data not shown). The most interesting observation was the broad spectrum that the 10 ppm silver composition possesses. The antimicrobial activity that was observed was fairly constant independent of the particular organism tested. With the exception of *Streptococcus faecalis* and *Streptococcus aureus* (which had MIC values of 10 ppm and 5 ppm, respectively), MIC values ranged between 1.25 ppm and 2.5 ppm for both gram positive and gram negative organisms. The MBC values behaved similarly with values ranging from 1.25 ppm to 5 ppm with the exception of *Streptococcus mutans, Streptococcus gordonii*, and *Streptococcus faecalis* (which all had MBC values of 10 ppm). The data suggest that 10 ppm silver embodiment of this invention exhibits an equal or broader spectrum of activity than any one antibiotic tested. Antibiotics generally have restricted antibacterial spectra limited to susceptible organisms, but as the data demonstrate, the silver composition of the present invention is equally effective against both gram positive and gram negative organisms. The data suggest that with the low toxicity associated with silver, in general, and the broad spectrum of antimicrobial activity of this silver composition, this preparation can be effectively used as an alternative to antibiotics.

D. Reference for Preceding Example

1 U.S. EPA IRIS Report for Silver-CASRN 7440-22-4

2 Fox C L, Modak S M. Mechanism of Silver Sulphadiazine Action on Burn Wound. Infections. Antimicrobial Agents Chemother. 5:582-588.1974.

3. Furchner, J E, Richmond C R, and G A Drake. Comparative Metabolism of Radionuclides in Mammals. IV. Retention of Silver-110m in the Mouse, Rat, Monkey, and Dog. Health Phys. 15:505-514.1968.

4. Grier, N. Silver and its Compounds in Disinfection, Sterilization, and Preservation. (Seymour S. Block, ed) $2^{nd}$ Edn, pp 395-407. 1977.

5. Hindler, J A, and J H Jorgensen. Procedure in Antimicrobial Testing in Diagnostic Microbiology. (CR Mahon and G Manuselis, eds) pp 63-91.1995.

Evidence of Efficacy of 32 ppm Silver Composition Against *Pseudomonas Aeruginosa, Salmonella Choleraesuis* and *Staphylococcus Aureus*

A. Methods

*Pseudomonas aeruginosa* ATTCC #15442, *Salmonella choleraesuis* ATTCC #10708 and *Staphylococcus aureus* ATCC #6538 were tested using the AOAC (Association of Official Analytical Chemists AOC Methods, vol. 1, $15^{th}$ edition, 1990, AOAC Arlington, Va.) official methods 955.14, 95515 and 964.02. Nutrient broth (NBAOAC) tubes were inoculated from the stock culture, and the tubes incubated at 37±2° C. Transfers to fresh tubes of nutrient broth were made for three successive days with the final transfer being incubated at 37±2° C. for 48-54 hr. The *Pseudomonas* culture was decanted into a fresh tube to remove the pellicle. The other cultures were vortexed for 3-4 seconds and allowed to stand for 10 min at room temperature. Finally the cultures were diluted 1:100 in peptone water (PEPW) to which equine serum was added to yield a 5% total organic challenge. Test carriers (10 mm long polished 304 stainless steel cylinders with an 8 mm outside diameter and 6 mm inside diameter) were soaked in challenge solution for 15 min, removed, drained and dried at 37±2° C. for 40±2 min prior to use.

Phenol Resistance.

Five-one ml aliquots of each dilution of the test phenol were placed into sterile test tubes and allowed to equilibrate in a 20±2° C. water bath. At 30 second intervals, 0.5 ml of each challenge culture was added to the appropriate dilutions of phenol, agitated, and replaced into the water bath: After the appropriate exposure times of 5, 10, and 15 minutes, a loopful of suspension was removed from the assay tubes and transferred to tubes of letheen broth (LETH). The tubes of LETH were incubated at 37±2° C. for 2 days.

Carrier Titration.

For titration of carriers, 10 ml blanks of peptone Tween® (brand of polysorbate) (PEPT) solution were prepared. Two carriers were placed into the individual tubes, representing the first 1:10 dilution. The tubes were agitated vigorously enough to get bacteria into solution and serial dilutions were made into 9 ml blanks of LETH medium. The dilution blanks were incubated at 37±2° C. The last tube with growth indicated the logo titer of organisms on the carrier. AOAC requires carriers to have minimum populations of $1 \times 10^4$ cfu/carrier.

Test of Silver Composition.

Using sterile glass pipettes, 10 ml aliquots of the prepared disinfectants were placed into sterile test tubes and allowed to equilibrate in a refrigerated water bath held at 20±2° C. Without touching the sides of the test tubes, one contaminated dried carrier was added at 30 second intervals to each tube of silver composition and placed back into the water bath. For each organism the disinfectant was tested against 60 dried contaminated carriers at 5 and 10 minute exposure intervals. Following exposure, the carriers were removed from the disinfectant and transferred to a tube of LETH. The culture tubes were incubated at 37±2° C. for 2 days and scored as positive (+) or negative (0) for growth of the challenge organism.

Controls.

For each organism, a dried contaminated carrier was added to a tube of LETH as a positive control. Uninoculated media tubes served as negative controls. After incubation, all negative tubes were spiked with 1-100 colony forming units (cfu) of the corresponding organisms to demonstrate neutralization efficacy. To demonstrate growth promotion of the media, the negative control tubes were also inoculated with the same 1-100 cfu for all three organisms. The inoculating volumes were plated in triplicate onto soybean casein digest agar (SCDA) to verify the inoculating titers. The tubes and plates were incubated at 37±2° C. until growth was seen in all tubes.

On the *P. aeruginosa* neutralization, the initial titer of inoculum was found to be >100 cfu which was too high for the protocol. Because all original tubes had been spiked, a simulated test was performed with same lot of media used in testing by placing carriers into disinfectant tubes from all three lots of silver compositions for 10 minutes. The carriers were sub-transferred to LETH blanks. These tubes were then spiked with 1-100 cfu of organism. The tubes were incubated as before and scored for growth or no growth. New tubes of sterile media from the same lot were also inoculated as a growth promotion verification.

B. Results

Initial testing using *S. aureus* demonstrated passing results for sample #1 and #2, but sample #3 failed. Upon investigation it was decided that sample #3 may have been damaged prior to shipment. A new bottle was obtained from the same lot as sample #3, and the new bottle was labeled as sample #4. The *S. aureus* challenge was repeated using sample #4. AOAC guidelines state that for any one time point and organism, only 1 carrier is allowed for growth for each lot tested.

Positive controls demonstrated growth and negative controls demonstrated no growth for all lots, time points, and organisms.

Carrier titration was run in duplicate for all organisms. The reported titer is an average of the replicates. For all three organisms, the average titer found on the carriers ranged from $5.5 \times 10^4$ to $5.5 \times 10^6$ cfu/carrier. AOAC requires carriers to have a minimum of $1.0 \times 10^4$ cfu/carrier.

For *P. aeruginosa* 3/180 carriers showed growth at the 5 min test point and 2/180 carriers showed growth at the 10 min test point. For *S. aureus* 16/180 carriers showed growth at the 5 min test point and 2/180 carriers showed growth at the 10 min test point. For *S. choleraesuis* 6/180 carriers showed growth at the 5 min test point and 1/180 carriers showed-growth at the 10 min test point.

The test *Pseudomonas* culture showed growth following a 5, 10 or 15 min treatment with 1:90 phenol and showed growth following a 5 or 10 min treatment with 1:80 phenol but no growth following 15 min treatment with 1:80 phenol. The *Staphylococcus* culture showed growth following a 5, 10 or 15 min treatment with 1:70 phenol and showed growth following 5 or 10 min treatment with 1:60 phenol but no growth following a 15 min treatment with 1:60 phenol. The *Salmonella* culture showed growth following a 5, 10 or 15 min treatment with 1:100 phenol but no growth following a 5, 10 or 15 min treatment with 1:90 phenol.

Evidence of Effectiveness of 32, 22, and 10 ppm Silver and 22 ppm Silver and 1.5% $H_2O_2$ and 10 ppm Silver and 10 ppm $K_2S_2O_8$ Against *Salmonella* and *Escherichia coli* in Freshly Inoculated Beef Samples A. Purpose of Example The purpose of this example is to demonstrate the antimicrobial activity of the silver-based composition embodiments of the present invention on samples of beef flank steak inoculated on the exterior surface with a five strain cocktail of *Salmonella* species. or *Escherichia coli* O157:h7 at a high inoculum solution level ($1 \times 10^6$ cfu/cm$^2$) and separately at a low inoculum solution level ($1 \times 10^4$ cfu/cm$^2$) (cfu=colony forming unit).

B. Material and Methods

Beef Samples.

Beef tissue samples were obtained from slaughter houses within 8 hours of evisceration. The rectus abdominus muscle was peeled off carcasses hanging in the chill cooler by making an incision between the 11$^{th}$ and 12$^{th}$ ribs and then peeling the muscle out along the natural seam. The aseptically retrieved samples were placed in plastic bags and on ice packs and were transported on the same day to the laboratory, where the samples were promptly packed in a Multi-Vac (A-300) and placed in a 4° C. cooler. Samples used for testing had a pH between 5.8 and 6.0 and were no more than 36 hours post evisceration. From randomly selected rectus abdominus muscles, 13×8 cm samples were cut and treated. After treatment, a 3.5 cm$^2$ flame sterilized stainless steel coring device and surgical scalpel were utilized to aseptically retrieve two meat cores per sampling interval from each sample. Tissue cores were placed in a sterile stomacher bag with 25 ml of 0.1% peptone and were mixed for two minutes in a stomacher (Lab Bender 400). Serial dilutions were prepared and spiral plated at 0 minutes, 20 minutes, 1 hour, 4 hours, and 24 hours post-treatment on selective and recovery media.

Bacterial Cultures.

Bacterial cultures were obtained from the Kansas State University (KSU) stock culture collection and were stored using the "Protected Bead" storage system. The following cultures were used for the *Salmonella* specimen: *S. lille* (UGA), *S. montevideo* (UGA), *S. typhimurium* (UGA), *S. agona* (KSU 05 from CDC outbreak isolate), and *S. newport* (KSU 06 CDC outbreak isolate). The following cultures were used for the *Escherichia coli* specimen: *E. coli* O157:H7 (CDC 01,03), *E. coli* O157:H7 (USDA-FSIS 011-82 Rif resistant 100 ppm), *E. coli* 157:H7 (ATCC 43895 HUS associated Type I & II toxins Rif. Res.) and *E. coli* ATCC#23740 (Genotype K-12 prototrophic lambda).

Stock cultures were cultivated by placing one impregnated bead into a 5 ml solution of Difco® Tryptic Soy Broth (TSB) and incubating for 24 hours at 35° C. Next, a 0.05 ml loop of the respective culture was inoculated into a 5 ml solution of TSB and incubated for 24 hour at 35° C. to obtain a pure culture. After incubation, 1 ml of the respective culture was inoculated into 49 ml TSB and incubated for 24 hours at 35° C. Following incubation, samples were centrifuged (15,300×g at 4° C.), and the supernatant material decanted and the pellet was re-suspended with 50 ml of 0.1% peptone and centrifuged (15,300×g at 4° C.) a final time. The peptone was decanted and the remaining pellet was re-suspended with 10 ml of 0.1% peptone. The five 10 ml bottles of respective culture were mixed together to create a 50 ml cocktail containing $10^9$ cfu/ml of *Salmonella* species. The cocktail was diluted to $10^6$ cfu/ml or $10^4$ cfu/ml using 0.1% peptone. Cultures were confirmed by cultivation on selective and differential media, and biochemical analysis of presumptive colonies using API 20E kits.

Method of Inoculation.

Samples of beef flank steak (rectus abdominus muscle) were trimmed to 13×8 cm (104 cm$^2$) and were inoculated with a five strain cocktail of *Salmonella* species. or *Escherichia coli* O157:h7 at a high inoculum solution level ($10^6$ log cfu/cm$^2$) and separately at a low inoculum solution level ($10^4$ log cfu/cm$^2$). This inoculum was misted onto the tissue surface using a plastic spray bottle with samples contained within a sealed inoculum chamber. The actual *Salmonella* species. concentration on the meat surface was approximately 5.0 and 3.4 log cfu/cm$^2$ for the high and low level inoculum solution, respectively. For *E. coli* O157:H7, the respective meat surface inoculation levels were 4.2 and 3.9 log cfu/cm$^2$.

The beef samples were then hung vertically on stainless steel hooks attached to a motorized track that pulled the beef samples through a model spray cabinet (Kansas State University, Food Safety Laboratory) while spray treatments were applied. Treatments with either the silver compositions of this invention or deionized water were applied to the beef at 20 psi from a distance of 13 cm in the model pressure rinse cabinet for 20 seconds. The spray nozzle (BETE NF0580 303) delivered approximately 20 ml of solution to the surface of the beef sample. The temperature of solutions and treatment application room was approximately 14° C. After treatment, duplicate 3.5 cm$^2$ core samples were randomly drawn from the lateral surface of the beef sample at 0, 20, 60 and 240 minutes. Samples were cultivated and enumerated on selective differential and recovery media. Log reductions were calculated by subtracting the $\log_{10}$ of cfu/cm$^2$ of the inoculated/treated samples at the specified sampling times (0, 20, 60, and 240 minutes) from the $\log_{10}$ of cfu/cm$^2$ of the inoculated/untreated samples at 0 minutes. Sample treatment included the use of 32 ppm silver, 22 ppm silver, and 10 ppm silver compositions according to the present invention. Separately, combinations of 22 ppm Ag with 1.5 wght % hydrogen peroxide and 10 ppm Ag with 10 ppm peroxydisulfate ($K_2S_2O_8$) were tested.

C. Results with 32 ppm Silver Composition

The use of a composition of 32 ppm silver according to this invention produced a reduction in bacteria on beef steak. In the following, this reduction is expressed as the $\log_{10}$ of the ratio of the number of bacteria in the control at time 0 to the amount of bacteria in the treated specimen at the sampling (i.e., treatment) time.

For *Salmonella*, at the lower initial bacteria level ($10^4$), the following log reductions were recorded: 0.78 at 0 minutes, 1.11 at 20 minutes, 1.08 at 60 minutes, and 1.23 at 240 minutes. Thus, at 4 hours (240 minutes), the ratio of the initial bacteria count in the control to bacteria in the sample treated with 32 ppm silver is $10^{1.23}$. For the higher initial bacteria level ($10^6$), the following log reductions were recorded: 0.86 at 0 minutes, 0.95 at 20 min, 0.98 at 60 min and 1.17 at 240 min. The results indicate that the 32 ppm silver embodiment of this invention shows an effective bactericidal effect for *Salmonella* on beef steak. It will be appreciated that disinfecting a meat surface is an extreme challenge for any disinfectant.

For *E. coli*, for the lower initial bacteria level ($10^4$), the following log reductions were recorded: 1.03 at 0 minutes, 1.28 at 20 minutes, 1.42 at 60 minutes, and 1.58 at 240 minutes. For the higher initial bacteria level ($10^6$), the following log reductions were recorded: 0.65 at 0 minutes, 0.60 at 20 minutes, 0.83 at 60 minutes and 0.87 at 240 minutes. The results indicate that the 32 ppm silver embodiment of this invention shows an effective bactericidal effect for pathogenic *E. coli* on beef steak.

D. Results with 22 ppm Silver Composition

Results with Silver in Water.

For *Salmonella* at the lower initial bacteria level ($10^4$), the following log reductions were recorded: 0.41 at 0 minutes, 0.43 at 20 minutes, 0.48 at 60 minutes, and 0.68 at 240 minutes. For the higher initial bacteria level ($10^6$), the following log reductions were recorded: 0.24 at 0 minutes, 0.24 at 20 minutes, 0.42 at 60 minutes and 0.61 at 240 minutes. The results indicate that the 22 ppm silver embodiment of this invention furnishes an effective bactericidal effect for *Salmonella* on beef steak.

Results with Silver in Water and 1.5 wght % Hydrogen Peroxide.

For *Salmonella*, for the lower initial bacteria level ($10^4$), the following log reductions were recorded: 0.34 at 0 minutes, 0.33 at 20 minutes, 0.36 at 60 minutes, and 0.62 at 240 minutes. For the higher initial bacteria level ($10^6$), the following log reductions were recorded: 0.28 at 0 minutes, 0.14 at 20 minutes, 0.30 at 60 minutes and 0.69 at 240 minutes. The results indicate that the 22 ppm silver with 1.5 wght % hydrogen peroxide embodiment of this invention provides an effective bactericidal effect for *Salmonella* on beef steak.

E. Results with 10 ppm Silver Composition

Results with Silver Composition, in Water.

For *Salmonella*, for the lower initial bacteria level ($10^4$), the following log reductions were recorded: 0.38 at 0 minutes, 0.41 at 20 minutes, 0.39 at 60 minutes, and 0.61 at 240 minutes. For the higher initial bacteria level ($10^4$), the following log reductions were recorded: 0.24 (at 0 minutes, 0.21 at 20 minutes, 0.41 at 60 minutes and 0.54 at 240 minutes. The results indicate that the 10 ppm silver embodiment of this invention provides an effective bactericidal effect for *Salmonella* on beef steak.

Results with Silver Composition in Water with 10 ppm $K_2S_2O_8$.

For *Salmonella*, for the lower initial bacteria level ($10^4$), the following log reductions were recorded: 0.26 at 0 minutes, 0.28 at 20 minutes, 0.35 at 60 minutes, and 0.58 at 240 minutes. For the higher initial bacteria level ($10^6$), the following log reductions were recorded: 0.03 at 0 minutes, 0.16 at 20 minutes, 0.21 at 60 minutes and 0.36 at 240 minutes. The results indicate that the 10 ppm silver with 10 ppm potassium peroxydisulfate ($K_2S_2O_8$) embodiment of this invention provides an effective bactericidal effect for *Salmonella* on beef steak.

Evidence of Effectiveness of 10 ppm Silver for Treatment of Human Ailments

A. Purpose of Example

The purpose of this example is to demonstrate the utility of silver-based composition embodiments of the present invention for treating a variety of human ailments. The studies in this section were performed in Ghana, West Africa, at the Air Force Station Hospital under the direction of Dr. Kwabiah, at the Korie-Bu Teaching Hospital under the direction of Sr. Sackey, and at the Justab Clinic/Maternity Hospital under the direction of Dr. Abraham. In total, fifty-eight (58) patients were treated using a composition of the present invention comprising 10 ppm silver. The composition was used both internally and externally as an alternative to traditional antibiotics. The ailments treated included malaria, upper respiratory tract infections, urinary tract infections, sinusitis, vaginal yeast infections, eye, nose and ear infections, cuts, fungal skin infections, and sexually transmitted diseases, such as gonorrhea.

B. Treatment Methods and Outcomes

Abdominal Pain and Diarrhea.

The method comprises the step of administering approximately 5-25 ml of silver composition, one to five times a day orally until there was a response. One patient was treated with about 10 ml (about two teaspoons) of a composition of the present invention three times in one day. The patient had a full recovery in one day.

Bronchitis.

The method comprises the step of administering ca. 2-25 ml of silver composition orally, one to five times a day until there was a response. Two patients were treated with about 5 ml (about one teaspoon) each of a composition of the present invention for two times a day for three days. The patients had a full recovery in three days.

Vaginal Yeast (*Candida*).

The method comprises the step of administering ca. 5-25 ml of silver composition, one to five times a day as vaginal douches until there was a response. Five patients were treated with about 10 ml (about two teaspoons) each of a composition of the present invention for two times per day. The patients showed a full recovery within six days.

Conjunctivitis.

The method comprises the step of administering ca. several drops of a silver composition, one to five times a day to the infected eye until there was a response. Two patients were treated with several drops of a composition of the present invention in each of the infected eyes for two times per day. The patients had a full recovery after one day.

External Cuts and Infection (Including *Staphylococcus* Skin Infections, Septic Ulcers and Infected Abscesses).

The method comprises the step of administering a silver composition, one to five times a day to the infected area until there was a response. Six patients were treated with about 5 ml (about one teaspoon) each of a composition of the present invention on the infected areas for two times per day. The patients showed a full recovery within three days.

External Otitis.

The method comprises the step of administering a silver composition, one to five times a day to the infected ear until there was a response. Six patients were treated with approximately two drops of a composition of the present invention into the infected ears for three times per day. The patients showed a full recovery after about four days.

Otitis Media.

The method comprises the step of administering a silver composition, one to five times a day to the infected ear until there was a response. One patient was treated with approximately two drops of a composition of the present invention comprising into the infected ear three times per day. The patient showed a full recovery in four days.

Fungal Skin Infection.

The method comprises the step of administering a silver composition, one to five times a day topically to the infected area until there was a response. Two patients were treated with about ten ml (two teaspoons) each of a composition of the present invention three times per day. The patients showed a full recovery within eight days.

Gonorrhea.

The method comprises the step of administering a silver composition to the infected area until there was a response. Two patients were each treated with about ten ml (two teaspoons) of a composition of the present invention three times per day. The patients showed an absence of symptoms within six days.

Malaria.

The method comprises the step of administering a silver composition, one to five times a day orally to the patient until there was a response. Eleven patients were treated with about ten ml (two teaspoons) each of a composition of the present invention three times per day. The patients showed a resolution of symptoms within five days.

Halitosis and Gingivitis.

The method comprises the step of administering a silver composition, one to five times a day as a mouthwash until there was a response. Two patients were each treated with the composition as a mouthwash. There was a full resolution of symptoms within three days (gingivitis) and within one day (halitosis).

Pelvic Inflammatory Disease.

The method comprises the step of administering about 5-25 ml of silver composition, one to five times a day as a vaginal douche until there was a response. One patient was treated with about 5 ml (approximately one teaspoon) of a composition of the present invention two times per day. The patient's symptoms resolved within five days.

Pharyngitis.

The method comprises the step of administering a silver composition, one to five times a day as a gargle until there was a response. Four patients were each treated with about ten ml (two teaspoons) of a composition of the present invention three times per day. The patients showed full recovery within six days.

Retrovirus Infection (HIV).

The method comprises the step of administering a silver composition, comprising 5 to 40 ppm silver one to five times a day orally area until there was a response. One patient exhibiting HIV (human immunodeficiency virus) was treated with about 5 ml (approximately one teaspoon) of a composition of the present invention two times per day. The patient's symptoms resolved within five days.

Sinusitis and Rhinitis.

The method comprises the step of administering a silver composition, one to five times a day to the nose until there was a response. Six patients with nasal infections (four with sinusitis and two with rhinitis) were each treated with approximately two drops of a composition of the present invention comprising in their nasal passages three times per day. The patients showed full recovery within four days.

Tonsillitis.

The method comprises the step of administering a silver composition, one to five times a day as a gargle until there was a response. One patient was treated with a composition of the present invention three times per day. The patient showed full recovery within seven days.

Upper Respiratory Tract Infection.

The method comprises the step of administering a silver composition, one to five times a day orally until there was a response. Two patients were each treated with about 5 ml (approximately one teaspoon) of a composition of the present invention three times per day. The patients showed full recovery within six days.

Urinary Tract Infections.

The method comprises the step of administering a silver composition, one to five times a day orally until there was a response. Three patients were each treated with about ten ml (two teaspoons) of a composition of the present invention two to three times per day. The patients showed full recovery within six days.

C. Discussion

These results are consistent with the various in vitro tests reported herein. Essentially, the silver composition is extremely effective against a large number of microbes in vitro. However, the tests indicate that this effectiveness remains even in the presence of a large amount of organic material. The silver compositions are widely effective in vivo where the organic background is extremely high. Many other disinfecting agents are ineffective in the presence of a large amount of organic material and/or are too caustic or toxic to be used in vivo.

Evidence of Efficacy of 10 ppm Silver Against Tuberculosis Bacteria

A. Purpose

The purpose of this example is to demonstrate the efficacy of a silver composition of the present invention against the bacteria that cause tuberculosis. This example describes the procedures for evaluation of the present invention for tuberculocidal efficacy. The methodology is based on the Tuberculocidal Activity Test Method as accepted by the EPA on Dec. 11, 1985. (Refer to United States Environmental Protection Agency, 1986. Office of Pesticides and Toxic Substances. Data Call-In Notice for Tubercuolocidal Effectiveness Data for All Antimicrobial Pesticides with Tuberculocidal Claims. (Received Jun. 13, 1986).

B. Material and Methods

Materials.

The silver composition of the present invention comprised 10 ppm silver in water. The silver composition was evaluated employing a liquid to liquid matrix against *Mycobacterium bovis* BCG (TMC 1028). This organism causes tuberculosis in animals and can cause tuberculosis in humans. It is used as a "stand-in" for *M. tuberculosis*, the major cause of human tuberculosis, as tests have shown it to have a similar susceptibility to *M. tuberculosis*. The test organism was exposed to the silver composition in duplicate at four exposure times and quantified using membrane filtration.

Procedure.

A vial of frozen stock culture was removed from storage and thawed. An equal volume of buffered gelatin (BUGE) was added to the cell suspension and homogenized with a Teflon® (brand of polytetrafluoroethylene) tissue grinder for 1 minute while keeping the culture at 0 to 4° C. in an ice bath. The homogenized cell suspension was diluted with saline Tween® 80 (brand of polysorbate) solution (ST80) to approximately $10^7$ cfu/ml.

Challenge Titration.

Tenfold serial dilutions of the culture were prepared in dilution blanks containing 9 ml of neutralizer broth (NEUB) through a $10^{-6}$ dilution. Three 1 ml aliquots of the appropriate dilutions were membrane filtered by first adding 10-20 ml physiological saline solution (PHSS) to the filter housing and then adding a 1 ml aliquot of the appropriate dilution. The filter was then rinsed with approximately 100 ml of PHSS.

The filters were aseptically removed from the filter housing and placed onto 7H11 agar plates. The plates were incubated in a humidified chamber at 37±2° C. for 21 days.

Positive Control.

A tube containing 9 ml of ST80 was prepared and equilibrated to 20±0.5° C. At time 0, 1 ml of test organism culture was added to the tube (1:10 dilution). The sample was held for 60 minutes. Tenfold serial dilutions were prepared in dilution blanks containing 9 ml of NEUB through $10^{-6}$-dilution. Three 1 ml aliquots of the appropriate dilutions were membrane filtered by first adding 10-20 ml PHSS to the filter housing and then adding a 1 ml aliquot of the appropriate dilution. The filter was rinsed with approximately 100 ml PHSS. The filters were aseptically removed from the filter housing and placed onto 7H11 agar plates. The plates were incubated in a humidified chamber at 37±2° C. for 21 days.

Tests.

Two 25×150 mm tubes containing 9 ml of the test sample were equilibrated to 20±0.5° C. in a water bath. To each tube containing the test disinfectant (i.e., silver composition), 1 ml of test organism culture was added. The tube was mixed by swirling and placed back into the water bath. At 15, 30, 45, and 60 minutes, 1.0 ml aliquots of the disinfectant-cell suspension were transferred to 9 ml of NEUB and mixed thoroughly. Tenfold serial dilutions were prepared in dilution blanks containing 9 ml of NEUB through the $10^{-6}$ dilution. Three 1 ml aliquots of the appropriate dilutions were membrane-filtered by first adding 10-20 ml PHSS to the filter housing and then adding a 1 ml aliquot of the appropriate dilution. The filter was rinsed with approximately 100 ml PHSS. The filters were aseptically removed from the filter housing and placed onto 7HII agar plates. The plates were incubated in a humidification chamber at 37±2° C. for 21 days.

Phenol Control.

To demonstrate minimum culture viability and resistance, the culture was tested against a 0.8% phenol solution. A 1 ml aliquot of test organism culture was placed into 9 ml of the phenol solution equilibrated to 25±0.5° C. and incubated for 20 minutes. After the exposure period, 1 ml from the phenol/organism solution was removed and added to 9 ml of NEUB. Tenfold serial dilutions were prepared in dilution blanks containing 9 ml of NEUB through $10^{-6}$ dilution. Three 1 ml aliquots of the appropriate dilutions were membrane filtered by first adding 10-20 ml PHSS to the filter housing and then adding a 1 ml aliquot of the appropriate dilution. The filter was rinsed with approximately 100 ml PHSS. The filters were aseptically removed from the filter housing and placed onto 7H11 agar plates. The plates were incubated in a humidified chamber at 37±2° C. for 21 days.

Neutralization Verification.

A 1 ml aliquot of the disinfectant was added to 8 ml of NEUB. The disinfectant/neutralizer broth was allowed to equilibrate to the same temperature as the test samples. One ml of test organism culture was added to the mixture and mixed thoroughly. Incubation was continued for the approximate time it would take to filter a sample. Additionally, a 1 ml aliquot of test organism was added to 9 ml of NEUB and mixed thoroughly (1:10 dilution). Tenfold serial dilutions of both tubes were prepared in dilution blanks containing 9 ml of NEUB thought $10^{-6}$ dilution. Three 1 ml aliquots of the appropriate dilutions were membrane filtered by first adding 10-20 ml PHSS to the filter housing and then adding a 1 ml aliquot of the appropriate dilution. The filter was rinsed with approximately 100 ml PHSS. The filters were aseptically removed from the filter housing and placed on 7H11 agar plates. The plates were incubated in a humidified chamber at 37±2° C. for 21 days.

C. Results

The starting titer for the challenge culture was $4.7 \times 10^7$ cfu/ml. The positive control titer was $6.5 \times 10^6$ cfu/ml. The media used in this study effectively demonstrated neutralization with a 95.2% recovery in a disinfectant/neutralizer solution when compared to a media blank.

For the test plates, expected counts were underestimated and therefore the reported counts exhibit ">" to mark that the count is an estimation and that accurate counts are beyond the limit of detection for the dilutions plated.

In calculating the log and percent reductions of the disinfectant against *M. bovis*, the estimated counts which have "greater than" counts resulted in "less than" log and percent reductions ("<"). The purpose of this is to demonstrate that the results are an estimation and beyond the accurate limit of detection for the dilutions plated. All reductions were calculated using the positive control as the initial starting titer of the organism. The results for log and percent reductions are summarized below. As a measure of the resistance of the challenge culture, the phenol resistance of the *M. bovis* showed a ~1.81 log reduction with 20 minutes of exposure to 0.8% phenol.

Replicate One:

| Exposure time | Log reduction | Percent reduction |
|---|---|---|
| 15 minutes | <0.12 | <12.3% |
| 30 minutes | <0.22 | <40.0% |
| 45 minutes | <1.57 | <97.2% |
| 60 minutes | <1.56 | <97.2% |

Replicate Two:

| Exposure time | Log reduction | Percent reduction |
|---|---|---|
| 15 minutes | <0.26 | <44.8% |
| 30 minutes | <0.20 | <36.9% |
| 45 minutes | <1.58 | <97.3% |
| 60 minutes | <1.53 | <97.1% |

D. Conclusions

The use of silver compositions of the present invention is effective against tuberculosis bacteria. A method comprising the step of administering silver compositions of the present invention is effective against tuberculosis organisms.

Evidence of Efficacy of 10 Ppm Silver Against *Candida Albicans* ATCC #10231, *Trichomonas Vaginalis* ATCC #20235, and MRSA *Staphyloccocus Aureus* ATCC #BAA-44

A. Purpose of Example

The purpose of this example is to illustrate the efficacy of silver compositions of the present invention against *Candida albicans* ATCC10231, *Trichomonas vaginalis* ATCC 20235, and drug resistant *Staphylococcus aureus* ATCC BAA-44.

*Candida albicans*, a yeast, and *Trichomonas vaginalisis*, a protozoa, can cause numerous health problems including vaginal infections, diaper rash, and thrush. The results below show that silver compositions of the present invention produced nearly a 100% kill of both organisms. The results show the utility of silver compositions of the present invention in a feminine hygiene product and in a diaper rash product.

*Staphylococcus aureus* can cause serious blood poisoning when it enters a wound. It once was easily treated with penicillin, but the organism has now mutated to the point where it is totally resistant to penicillin. The next defense on the antibiotic ladder has been methicillin, but methicillin-resistant strains have become increasingly common, especially in hospitals. These strains are known as MRSA (methicillin-resistant *Staphylococcus aureus*) and have been dubbed the "superbug." People who contract MRSA can die in a matter of days. In the results reported in this example, a silver composition of the present invention was found to kill 91.6% of the MRSA in just 10 minutes, and 99.5% in an hour. The results show the utility of silver compositions of the present invention in killing MRSA, a known infectious threat.

B. Methods and Results

Employing the USP Preservative Rapid Challenge Test with a composition of the present invention comprising 10 ppm silver in water, the following results were obtained. These results show that silver compositions of the present invention can be effective against yeast infections, protozoa infections, and drug resistant bacteria infections.

*Candida albicans* ATCC #10231.

The initial concentration of *Candida albicans* yeast was $6.8\times10^5$ cfu/ml. After contact for either 10 minutes, 30 minutes, 1 hour, or one day with the silver composition, there were no colonies detected.

*Trichomonas vaginalis* ATCC #30235.

The initial concentration of *Trichomonas vaginalis* protozoa was $6.0\times10^4$ cfu/ml. After contact with the silver composition for either 10 minutes, 30 minutes, 1 hour, or one day, there was 0% motility of 100 Organisms. That is, one hundred (100) *Trichomonas vaginalis* parasites were analyzed via microscopy for motility of flagella. None of the one-hundred (100) parasites demonstrated motility after only ten (10) minutes of contact with the silver composition indicating inhibitory or lethal properties of the silver composition on the parasites. The outer membranes of twenty-five (25) percent of the parasites had ruptured after contact of one (1) day.

*Staphylococcus aureus* MRSA ATCC #BAA-44.

The initial concentration of methicillin-resistant *Staphylococcus aureus* (MRSA) was $6.0\times10^6$ cfu/ml. After contact with the silver composition, there were 500,000 cfu/ml detected after 10 minutes contact (91.6% killed), 70,000 cfu/ml after 30 minutes contact (98.8% killed), 30,000 cfu/ml after 1 hour contact (99.5% killed), and fewer than 10 cfu/ml after one day contact (virtually total kill).

Evidence of the Efficacy and Lack of Cytotoxicity of 10 ppm Silver, 14 ppm Silver+1.5% $H_2O_2$, and 22 ppm Silver in Inhibiting DNA Polymerase and Reverse Transcriptase in the Context of Hepatitis B A. Purpose of Example The purpose of the example is to illustrate the efficacy of silver compositions of the present invention against hepatitis B. This example shows that silver compositions of the present invention have antiviral properties. Any agent used in antiviral therapy should exhibit little or no cytotoxicity so cytotoxicity of the silver compositions was analyzed.

Hepatitis B is caused by a DNA virus of the hepadnaviridae family of viruses. The Hepatitis B Virus (HBV) is a 3.2 kb DNA virus, replicating almost exclusively in the liver cells (hepatocytes). Replication involves two main enzymes: DNA polymerase and reverse transcriptase. The results of this example show that silver compositions of the present invention interfere with replication involving either DNA polymerase or reverse transcriptase. The results of this example show that silver compositions of the present invention have antiviral properties. The results of this example show that silver compositions of the present invention can be effective against hepatitis B.

As further detail, when hepatitis B enters the body of a new host, it infects the liver if it gets past the host's immune system. In the infection, the virus attaches to the membrane of a liver cell, and the core particle of the virus enters the liver cell. The core particle then releases its contents of DNA and DNA polymerase into the liver cell nucleus. Within the liver cell, the virus replicates via reverse transcription and translation processes, which involve reverse transcriptase and DNA polymerase enzymes. The DNA polymerase causes the liver cell to make copies of hepatitis B DNA. These copies of the virus are released from the liver cell membrane into the blood stream. From there, they can infect other liver cells and thus replicate effectively. The incubation period of the hepatitis B virus is about 6 to 25 weeks (i.e., time before physical and generally detectable histological or physical symptoms occur). However, there are several biochemical and histological changes that occur in the early stages following infection with the hepatitis B virus.

B. Materials

Solutions comprising 10 ppm, 14 ppm, 22 ppm, and 32 ppm silver compositions according to the present disclosure were used. The nucleotides dATP, dGTP, dCTP, and [$^3$H]-dTTP were obtained from standard commercial sources, as were the compounds lamivudine (a synthetic antiretroviral agent) and zidovudine (AZT). Isolated Hepatitis B virus was freshly obtained from a person suffering from Hepatitis B infection and was taken up by Haffine Institute, Mumbai INDIA (a WHO certified testing laboratory). Test cell cultures (Vero and Hep2) were grown as confluent monolayers by typical cell culture methods.

C. Methods

1) Procedure for Test of DNA Polymerase Inhibition.

Overall Approach.

Hepatitis B viral extracts from human subjects are incubated with radiolabelled nucleotides and an active inhibitor. Percent inhibition is calculated based on the amount of de novo viral nucleic acid synthesized with respect to lamivudine as a positive control and phosphate buffer saline (PBS) as a negative control.

Specific Procedure.

Isolated Hepatitis B virus was lysed to extract free polymerase enzyme, which is free from contaminating enzymes. A virus extract (25 μl) was added to a reaction mixture comprising dATP, dGTP, dCTP and [$^3$H]dTTP nucleotides (25 μl). Active inhibitor (3 μl) was added to the mixture comprising virus extract and nucleotides. The resultant mixture was incubated at 37° C. for 2 hours.

A separate negative control experiment was performed in which phosphate buffer saline (PBS, 3 μl) was used instead of the inhibitor (3 μl).

A separate positive control experiment was performed in which a known DNA polymerase inhibitor (3 μl of lamivudine at a concentration 3 mg/ml) was used instead of the tested inhibitor (3 μl).

The reaction was stopped by adding 25 μl EDTA and 25 μl TCA (trichloroacetic acid). The reaction mixture was then spotted on ionic paper (DEAE paper). The paper was washed three times with TCA and then with ethyl alcohol. The filter paper was air dried and put into a scintillation vial with a scintillation cocktail. Radioactivity was measured by a liquid scintillation counter (Blue Star). As a counting control, a blank silver composition was run through the complete procedure without viral load, to check any potential interference in the scintillation counter method.

A reference for this method is P. S. Venkateswaran, I. Millman, and B. S. Blumberg, "Effect of an extract from *Phyllanthus niruri* on hepatitis B and woodchuck hepatitis viruses: in vitro and in vivo studies," Proc. Natl. Acad. Sci., USA, 1987, 84, 274-278, which is incorporated herein by reference.

2) Procedure for Test of Reverse Transcriptase Inhibition.

A commercial viral enzyme preparation of Moloney murine leukemia virus reverse transcriptase (MoMuLV) having Poly(A)dT (primer for RT) was used. 50 µl of the MoMuLV preparation was combined with a mixture of dATP, dGTP, dCTP and [$^3$H]dTTP nucleotides.

This mixture was combined with 3 µl of the inhibitor to be tested, and the resultant mixture was incubated at 37° C. for 2 hours.

A negative control experiment was performed in which phosphate buffer saline (PBS, 3 µl) was used instead of the inhibitor.

A positive control experiment was performed in which a known reverse transcriptase inhibitor (3 µl of AZT at a concentration 0.625 microgram/ml) was used instead of the tested inhibitor.

The reaction was stopped by adding 25 µl EDTA and 25 µl TCA. The reaction mixture was then spotted on ionic paper (DEAE paper). The paper was washed three times with TCA and then with ethyl alcohol. The filter paper was air dried and put in a scintillation vial with a scintillation cocktail. Radioactivity was measured by a liquid scintillation counter (Blue Star).

3) Procedure for Testing Cytotoxicity.

Cells were prepared from healthy, confluent Vero and Hep2 cell cultures that were maintained by passage every 3-4 days. One day prior to the test cells were released from the cultures using standard techniques and suspended in a growth medium and dispensed into wells of a microtiter plate and placed in a 5% $CO_2$ incubator at 37±2° C. An aliquot (100 µl) of each test substance was introduced into a well (in triplicate) with 100 µl of PBS as a control. Every 24 hrs the wells were examined under high power of an inverted microscope to check for any cytopathic effect (CPE).

D. Results

Results for Test of Reverse Transcriptase Inhibition:

| Sample | % Inhibition |
| --- | --- |
| negative control (PBS) | 0 |
| positive control (AZT) | 31.33 |
| Silver, 10 ppm | 89.52 |
| Silver, 14 ppm and 1.5% H2O2 | 86.93 |
| Silver, 22 ppm | 84.46 |

Results for Test of DNA Polymerase Inhibition:

| Sample | % Inhibition |
| --- | --- |
| negative control (PBS) | 0 |
| positive control (lamivudine) | 31.33 |
| Silver, 10 ppm | 77.73 |
| Silver, 14 ppm with 1.5% H2O2 | 65.6 |
| Silver, 22 ppm | 60.89 |

Silver Compositions of the Present Invention are Highly Effective at Inhibiting DNA Polymerase Results for Test of Reverse Transcriptase Inhibition:

| Sample | % Inhibition |
| --- | --- |
| negative control (PBS) | 0 |
| positive control (AZT) | 18.06 |
| Silver, 10 ppm | 89.52 |
| Silver, 14 ppm with 1.5% H2O2 | 86.93 |
| Silver, 22 ppm | 84.46 |

Thus, silver compositions of the present invention inhibit reverse transcriptase. Silver compositions of the present invention would be expected to be effective against human ailments propagated by viruses, such as hepatitis B.

Results for Test of Cytotoxicity:

| Sample | Vero | Hep2 |
| --- | --- | --- |
| control (PBS) | No CPE | No CPE |
| Silver, 10 ppm | No CPE | No CPE |
| Silver, 14 ppm with 1.5% H2O2 | CPE positive | CPE positive |
| Silver, 22 ppm | No CPE | No CPE |

These results indicate that the silver composition is essentially non-cytotoxic. As expected, hydrogen peroxide, which is known to be cytotoxic, shows a cytotoxic effect. Thus, the silver should be harmless to cells when used in vivo.

12. Evidence of Efficacy of Silver Composition as Water Disinfectant

A. Purpose

Tests were carried out to demonstrate the efficacy of the inventive composition in disinfecting drinking water.

B. Methods

A sample of raw river water was spiked with two loopfuls of *Klebsiella oxtyoca*. 100 ml aliquots of this of this spiked water solution were brought to 0.05 ppm, 0.1 ppm, 0.2 ppm, 0.5 ppm, or 1.0 ppm of inventive silver composition. After an incubation of 5-60 minutes, the samples were membrane filtered. The filter was rinsed with approximately 100 ml sterile water. The filters were aseptically removed from the filter housing and placed on coliform nutrient agar plates. The plates were incubated under growth conditions for 24 hours and counted.

| Sample | Silver (ppm) | Contact (min) | Total Coliform (per ml) | Cfu/100 ml |
| --- | --- | --- | --- | --- |
| raw water | — | — | 36 | TNTC |
| 1 | 1.00 | 5.0 | 0 | 0 |
| 2 | 1.00 | 10.0 | 0 | 0 |
| 3 | 1.00 | 15.0 | 0 | 0 |
| 4 | 1.00 | 30.0 | 0 | 0 |
| 5 | 0.50 | 10.0 | 0 | 0 |
| 6 | 0.50 | 30.0 | 0 | 0 |
| 7 | 0.50 | 60.0 | 0 | 0 |
| 8 | 0.20 | 5.00 | 0 | 0 |
| 9 | 0.20 | 10.0 | 0 | 0 |
| 10 | 0.20 | 30.0 | 0 | 0 |
| 11 | 0.20 | 60.0 | 0 | 0 |
| 12 | 0.10 | 10.0 | 0 | 0 |
| 13 | 0.05 | 20.0 | 0 | 0 |

TNTC = too numerous to count.

The silver composition proved to be surprisingly effective. Even at the shortest time (20 min) allowed for incubation of the lowest concentration tested (0.05 ppm) there was a complete kill of the bacteria. At 0.20 ppm and higher there was a complete kill at 5 minutes. It seems clear that a complete kill takes less than 5 minutes.

Evidence of Efficacy of 32 ppm Silver as Surface Disinfectant

The Environmental Protection Agency (EPA) has approved a 32 ppm silver composition of the present invention as a broad spectrum surface disinfectant for use in hospitals, medical environments, residential homes, commercial buildings, and businesses. It has been approved for use against some of the most deadly pathogens including: Gram-positive bacteria, such as Staphylococcus aureus (presently considered to be the most deadly bacteria in U.S. hospitals), Gram-negative bacteria, such as Salmonella choleraesuis (responsible for food poisoning), and nosocomial or hospital-acquired pathogens, such as Pseudomonas aeruginosa (often found in burns and cuts).

Silver compositions of the present invention can be sprayed in and around occupied areas without endangering the lives of people. One can disinfect surfaces selected from the group consisting of walls, tables, chairs, light fixtures, bathrooms, glass, porcelain, metal, glazed ceramic, enameled and painted by means of spraying or by means of wiping with a silver composition of the present invention. A preferred method of disinfecting comprises one or more of the steps of cleaning the surface to be disinfected, applying, by means of a spray, mop, sponge, or cloth, a composition of the present invention, thoroughly wetting the area to be disinfected, allowing the surface to remain wet for at least 10 minutes at a temperature of at least 20° C. (time/temperature interrelation can be adjusted via the Arrhenius equation or other means known to one of ordinary skill), and wiping the surface with a clean paper or cloth towel. Compositions for disinfecting surfaces comprise those comprising 5 to 40 ppm silver. A preferred composition of the present invention for disinfecting surfaces comprises (32±3) ppm silver. Another preferred composition of the present invention for disinfecting surfaces comprises (10±2) ppm silver. Another preferred composition of the present invention for disinfecting surfaces comprises (22±2) ppm silver.

Evidence of Efficacy of Silver Composition as Super Disinfectant

A. Purpose of Example

The purpose of this example is to show the antimicrobial activity of a silver composition of the present invention (here 10 ppm silver, 14 ppm silver with 1.5 wght % hydrogen peroxide, and 32 ppm silver) against the test organism Yersinia pestis, the etiologic agent of bubonic plague. By performing a standard kill-time assay using a Y. pestis suspension, it is demonstrated that silver compositions of the present invention are effective even against the bubonic plague bacteria.

B. Material and Methods

Y. Pestis, strain D27, was grown on a Columbia Agar plate for about 24 hours at 30° C. in a 5% $CO_2$ incubator. Growth from the plate was scraped into suspension, using 3 ml of sterile HPLC water. The suspension was transferred to a 50 ml conical centrifuge tube. The plate was then rinsed using an additional 2 ml of HPLC water. This rinse was added to the centrifuge tube. The tube was centrifuged at 3,500×g for 5 minutes. The supernatant was discarded and the pellet was resuspended in 1 ml of HPLC water, to give a final concentration of approximately $10^{10}$ cells per ml.

The method involved the following steps:

1 A 9.9 ml aliquot of the silver composition to be tested was placed in a sterile 20 mm×150 mm tube. The tube was equilibrated in a 20° C. water bath.

2 The tube of silver composition was inoculated with 100 μl of the test organism suspension at time zero to form a mixture. The tube was immediately vortexed and returned to the water bath.

3 At 2 min, 3 min, 4 min, and 5 min for 10 ppm or 32 ppm silver or 2 min, 4 min, 6 min and 8 min for 14 ppm silver with 1.5% v/v $H_2O_2$, 1 ml of organism/silver mixture was removed to 99 ml of neutralizer in a 250 ml Erlenmeyer flask. The flask was mixed thoroughly.

4 The neutralized suspension was immediately serially diluted 1:10 in physiological saline solution (PSS).

5 The number of viable organisms in selected dilution tubes and flasks was assayed by membrane filtration. One ml aliquots were plated in duplicate. The membranes were washed with about 150 ml (or 250 ml if the sample was taken from the neutralizer flask) of sterile phosphate buffered saline and removed to Columbia Agar plates. The entire remaining contents (98 ml) of the 4 & 5 min neutralizer flasks were also plated. The plates were incubated at 30° C. in a 5% $CO_2$ incubator for 72 hours.

6 The number of colonies on each filter was counted and log reductions were computed.

C. Results

The results for 10 ppm silver are as follows:

| Time | Log Reduction | Percent Kill |
| --- | --- | --- |
| 2 min | 2.63 | 99.77 |
| 4 min | 3.20 | 99.94 |
| 6 min | 3.46 | 99.97 |
| 8 min | 3.68 | 99.98 |

The calculated regression equation for these data is Y=2.3965+0.1696x. This indicates that the time for a 6-log reduction is 21.2 minute.

The results for 32 ppm silver are as follows:

| Time | Log Reduction | Percent Kill |
| --- | --- | --- |
| 2 min | >7.61 | 99.999998 |
| 4 min | >7.61 | 99.999998 |
| 6 min | >7.61 | 99.999998 |
| 8 min | >7.61 | 99.999998 |

The results for 14 ppm silver with 1.5% v/v $H_2O_2$ are as follows:

| Time | Log Reduction | Percent Kill |
| --- | --- | --- |
| 2 min | 3.27 | 99.95 |
| 3 min | 4.72 | 99.998 |
| 4 min | 5.36 | 99.9996 |
| 5 min | 6.47 | 99.99997 |

The calculated regression equation for these data is Y=1.371+1.024x. This indicates that the time for a 6-log reduction is 4.52 minute.

The silver composition of the present invention exhibited significant bactericidal activity against Y. pestis, the etiologic agent of bubonic plague. The 32 ppm composition gave more than a 7 log reduction (essentially total kill) in less than 2 min.

The data show that the 10 ppm silver takes some 20 min to achieve a 6 log kill. The silver and hydrogen peroxide show significant synergism with a calculated 6 log kill of under 5 min. This is much better than 10 ppm silver alone. The level of 14 ppm silver was chosen because the data of other experiments suggested that this level of silver combined with hydrogen peroxide would achieve results approaching those of the 32 ppm silver product.

Data Summary

The following table contains a summary of the above results in terms of the effects of the inventive silver composition on a wide variety of microbes and human diseases. In some cases, the data presented in the table is not repeated above. However, the results were obtained using the procedures explained above so that one of ordinary skill in the art can readily replicated the results.

Human Diseases Cured by and Pathogens Killed by the Inventive Silver Composition:

| Disease | Pathogen | Effective Concentration |
| --- | --- | --- |
| Boils | Staphylococcus aureus | Killed @ 5 ppm |
| Osteomyelitis | Staphylococcus aureus | Killed @ 5 ppm |
| Bacillary Dysentery | Shigella boydii | Killed @ 2.5 ppm |
| Burn Infections | Pseudomonas aeruginosa | Killed @ 5 ppm |
| Dental Plaque | Streptococcus mutans | Killed @ 5 ppm |
| Diarrhea (Bloody) | Shigella boydii | Killed @ 2.5 ppm |
| Diarrhea | Escherichia coli | Killed @ 2.5 ppm |
| Ear Infection | Haemophilus influenzae | Killed @ 1.25 ppm |
| Ear Infection | Streptococcus pneumonie | Killed @ 2.5 ppm |
| Enteric Fever | Salmonella tyhimurium | Killed @ 2.5 ppm |
| Epiglottitis (In children) | Haemophilus influenzae | Killed @ 1.25 ppm |
| Eye Infections | Staphylococcus aureus | Killed @ 5 ppm |
| Corneal Ulcers-Keratitis | Pseudomonas aeruginosa | Killed @ 5 ppm |
| Food Poisoning | Salmonella arizona | Killed @ 5 ppm |
| Food Poisoning | Salmonella tyhimurium | Killed @ 2.5 ppm |
| Food Poisoning | Escherichia coli | Killed @ 2.5 ppm |
| Endocarditis | Streptococcus faecalis | Killed @ 2.5 ppm |
| Endocarditis | Streptococcus gordonii | Killed @ 5 ppm |
| Meningitis | Haemophilus influenzae | Killed @ 1.25 ppm |
| Meningitis | Enterobacter aerogenes | Killed @ 2.5 ppm |
| Meningitis | Pseudomonas aeruginosa | Killed @ 5 ppm |
| Meningitis | Streptococcus pneumonie | Killed @ 2.5 ppm |
| Nosocomial Infections | Klebsiella pneumoniae | Killed @ 2.5 ppm |
| Nosocomial Infections | Pseudomonas aeruginosa | Killed @ 5 ppm |
| Nosocomial Infections (From hospitals) | Streptococcus pyogenes | Killed @ 1.25 ppm |
| Pneumonia | Staphylococcus aureus | Killed @ 5 ppm |
| Pneumonia | Haemophilus influenzae | Killed @ 1.25 ppm |
| Pneumonia | Pseudomonas aeruginosa | Killed @ 5 ppm |
| Pneumonia | Streptococcus pneumonie | Killed @ 2.5 ppm |
| Respiratory Tract Infections | Streptococcus pyogenes | Killed @ 1.25 ppm |
| Respiratory Tract Infections | E. coli | Killed @ 2.5 ppm,, |

| Disease | Pathogen | Effective Concentration |
| --- | --- | --- |
| Respiratory Tract Infections | Klebsiella pneumoniae | Killed @ 2.5 ppm |
| Scarlet Fever | Streptococcus pyogenes | Killed @ 1.25 ppm |
| Septicemia | Enterobacter aerpyogenes | Killed @ 2.5 ppm |
| Sinus Infections | Haemophilus influenzae | Killed @ 1.25 ppm |
| Sinusitis | Streptococcus pneumonie | Killed @ 2.5 ppm |
| Impetigo | Staphylococcus aureus | Killed @ 1.25 ppm |
| Skin Infections | Staphylococcus aureus | Killed @ 5 ppm |
| Skin Infections | Streptococcus pyogenes | Killed @ 1.25 ppm |
| Strep Throat | Streptococcus pyogenes | Killed @ 1.25 ppm |
| Suppurative Arthritis | Haemophilus influenzae | Killed @ 1.25 ppm |
| Throat Infections | Haemophilus influenzae | Killed @ 1.25 ppm |
| Tooth Decay | Streptococcus mutans | Killed @ 5 ppm |
| Urethritis (Men) | Trichomonas vaginalis | Killed @ 10 ppm |
| Urinary Tract Infections | E. coli | Killed @ 2.5 ppm |
| Urinary Tract Infections | Klebsiella pneumonias | Killed @ 2.5 ppm |
| Urinary Tract Infections | Pseudomonas aeruginosa | Killed @ 5 ppm |
| Urinary Tract Infections | Streptococcus faecalis | Killed @ 2.5 ppm |
| Urinary Tract Infections | Enterobacter aerpyogenes | Killed @ 2.5 ppm |
| Vaginitis (Women) | Trichomonas vaginalis | Killed @ 10 ppm |
| Wound Infections | Escherichia coli | Killed @ 2.5 ppm |
| Wound Infections | Enterobacter aerpyogenes | Killed @ 2.5 ppm |
| Wound Infections | Klebsiella pneumoniae | Killed @ 2.5 ppm |
| Wound Infections | Pseudomonas aeruginosa | Killed @ 5 ppm |
| Wound Infections | Streptococcus faecalis | Killed @ 2.5 ppm |
| Yeast Infections | Candida albicans | Killed @ 10 ppm |

Efficacey of Silver Colloid Formulated as a Hydrogel

Modern wound care has come to recognize the fact that for optimal healing a wound should be kept sterile and protected from desiccation and environmental contaminants. Traditional bandages are effective as providing protection from environmental contaminants but are largely ineffective at preventing desiccation. Bandages may be rendered antimicrobial through the addition of a variety of disinfectant substances, but these substances are often harsh and kill cells or the body as well as microbes. In recent times wound care has been revolutionized by hydrogel materials which are available as either a semisolid (amorphous material) or as a soft sheet-like material. The hydrogel is hydrophilic and hence prevents desiccation of the wound. The sheet-like material is effective at excluding environmental contaminants and because of its hydrophilic character, the hydrogel can actually absorb excess fluid exuded by the wound.

Hydrogels are formed by combining a hydrophilic polymer with other ingredients in an aqueous solution. The polymer forms a gel following a change in pH, temperature or other triggering event. In a gel a fine molecular network of the polymer surrounds regions of the aqueous solution. Although the composition may be an amorphous semi-solid or a firmer sheet-like material, the vast majority of the volume tends to be occupied by the aqueous solution as opposed to the hydrophilic polymer. Hydrophilic polymers that are appropriate for the production of hydrogels include gelatin, carboxy-methyl cellulose (and other cellulose derivatives), other carbohydrate polymers of plant or algal origin such as alginate, carrageenan, xanthan gum, locust bean gum, gum traganth, guar gum, gum arabic and other plant gums, acrylic acid copolymers (such as Carbopol), and combinations of these and similar hydrophilic polymers.

The aqueous component preferably contains various additive substances that enhance the physical characteristics of the hydrogel and/or enhance wound healing. These include various vitamins, amino acids and growth factors added to enhance healing or reduce scar formation to diminish scarring. Common anesthetics such as novocaine, lidocaine and derivatives thereof can also be incorporated as additives to enhance comfort. Since keeping the wound sterile is a major goal of the dressing, various antimicrobial or disinfectant agents are advantageously included. These include organic acids such as citric acid, dilute acetic acid, benzoic acid, proprionic acid and lactic acid. Alcohols such as isopropanol or ethanol are useful as are organic disinfectants including chlorinated phenolics such as "TCP" (2,4,6 trichlorophenol), biguanides, chlorhexidine (when mixed with cetrimide), chlorhexidine gluconate, and chlorhexidine acetate. Disinfectant surfactants including amphoteric surfactants and aldehydes such as formaldehyde and glutaraldehyde can be included. Halogen disinfectants including iodine, iodophores, and polyvidone-iodine are effective as are peroxides and other oxygenators such as hydrogen peroxide. Other beneficial ingredients include aluminum-zinc astringent agents, furan derivatives and quinoline derivatives such as clioquinol. As beneficial as all these antimicrobial agents may be, they all tend to suffer from the defect that they can be damaging to tissue and/or microbes can readily develop resistance to them.

As amply demonstrated above, the inventive silver colloid is highly effective antimicrobially, is very gentle to human tissue and is effective against resistant microbes. Both amorphous gel and hydrogel sheet are both amenable to delivering effective levels of colloidal silver in moist healing environment. On one hand the amorphous hydrogel slowly releases colloidal silver as it slowly softens in tissue exudate and gradually begins to dissolve. On the other hand amorphous hydrogel donates moisture to the tissue and simultaneously makes colloidal silver available at site. In addition, a small amount of colloidal silver present in the dressing has the advantage of being molecular silver, whose gradual reduction over an extended period of time will release silver ions which have excellent oligodynamic activity.

After initial experiments Carbopol was selected as an effective hydrogel forming agent for use with the inventive colloidal silver. A basic formulation was developed which generally included the following ingredients:

| Ingredient | Function | Supplier |
|---|---|---|
| Colloidal Silver Solution (22 ppm or 32 ppm) | Active, Anti-microbial & Diluent | American Biotech Labs |
| Carbopol ETD2020 | Rheology Modifier | Noveon |
| Triethanolamine | Neutralizer, Penetrating agent | E. Merck |
| Propylene Glycol | Humectant | E. Merck |

All raw materials were first analyzed for

1. Anti-bacterial Activity
2. Physical & Chemical Properties:
    1. Appearance
    2. Odor
    3. pH
    4. Feel
    5. Density
    6. Foaming Property
    7. Flow-ability.

Colloidal Silver Solution (22 ppm or 32 ppm):

In this formulation Silver Solution is used as an active component (anti-microbial agent). It is also the only diluent in this specific formulation.

A. Anti-Bacterial Activity:

| | Diameter of zone of inhibition | |
|---|---|---|
| Culture | 22 ppm | 32 ppm |
| MRSA | 17 mm | 18 mm |
| E. coil | 14 mm | NA |
| Ps. aeruginosa | 21 mm | 22 mm |

B. Physical & Chemical Properties:

| 1. | Appearance | Colorless clear liquid |
|---|---|---|
| 2. | Odor | Odorless |
| 3. | pH | 5.0 |
| 4. | Feel | Not Applicable |
| 5. | Density | 1.00 |
| 6. | Foaming Property | Not Applicable |
| 7. | Flow-ability | Not Applicable |

Carbopol

Carbopol is chemically known as carboxypolymethylene or carboxyvinyl polymer. It is a copolymer of acrylic acid and is highly ionic (i.e., hydrophylic) and slightly acidic compound. Carbopol polymers must be neutralized in order to achieve maximum viscosity. It is used in pharmaceuticals, cosmetic & textile printing fields as a thickening, suspending, dispersing and emulsifying agent. In this formulation Carbopol is used as a gelling or thickening agent.

A. Anti-Bacterial Activity Not Applicable

B. Physical & Chemical Properties:

| 1. | Appearance | Dry, white powder |
|---|---|---|
| 2. | Odor | Odorless |
| 3. | pH | Not Applicable |
| 4. | Feel | Not Applicable |
| 5. | Density | Not Applicable |
| 6. | Foaming Property | Not Applicable |
| 7. | Flow-ability | Not Applicable |

Triethanolamine (TEA) $C_6H_{15}NO_3$ (Mol. Wt.: 149.19)

In this formulation Triethanolamine, an alkalizing agent neutralizes Carbopol to raise the viscosity. It also increases the penetrating power of the active agent.

A. Anti-Bacterial Activity (Not Applicable)

B. Physical & Chemical Properties

| 1. | Appearance | Colorless viscous liquid |
|---|---|---|
| 2. | Odor | Slight ammoniacal |
| 3. | pH | Not Applicable |
| 4. | Feel | Not Applicable |
| 5. | Density | 1.1242 g/cc |
| 6. | Foaming Property | Not Applicable |
| 7. | Flow-ability | Not Applicable |

Propylene Glycol $C_3H_8O_2$ Mol. Wt.: 76.09

Propylene Glycol is chemically known as 1:2 propanediol. It is used as a humectant and feel modifier in this formulation.

A. Anti-Bacterial Activity Not Applicable
B. Physical & Chemical Properties:

| | | |
|---|---|---|
| 1. | Appearance | Colorless viscous liquid |
| 2. | Odor | Odorless |
| 3. | pH | Not Applicable |
| 4. | Feel | Not Applicable |
| 5. | Density | 1.036 gm/cc |
| 6. | Foaming Property | Not Applicable |
| 7. | Flow-ability | Not Applicable |

Once the standard formula was developed a number of batches were manufactured to explore the possible range of formulations. From the 19 experiments carried out the following observation were reached.
1. Increase in pH increases viscosity of gel.
2. Increase in Carbopol quantity increases viscosity of gel.
3. Higher the Carbopol percentage the higher the tackiness.
From the above experiments it can be concluded that a trade off has to be reached between amount of Carbopol & TEA used and the final pH obtained which should not be more than 8.5. Hence formulation No. 18 was kept as standard and batch scaled up to 10 Kg.

Product Development Studies Introduction:

Carbopol based gel formulations have to be standardized with respect to pH, feel, tackiness and consistency. With this in mind various lab batches were taken using water as the aqueous phase to obtain a product of suitable quality and feel before taking the main batch.

| | Batch No. SG/001 Formulation: | |
|---|---|---|
| Part A: | Distilled Water | 83.50 g |
| | Carbopol | 00.62 g |
| | NaOH 18% | 00.60 g |
| Part B: | Distilled Water | 1.00 g |
| | Propylene glycol | 5.00 g |
| | NaOH 18% | 1.50 g |

Procedure: Weigh the given amount of Distilled Water from Part A and keep in water bath at 70° C. Add Carbopol to Distilled Water with constant stirring to avoid lumps. Add NaOH 18% to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results: | 1. pH | 10.8 |
|---|---|---|
| | 2. Flow-ability | 90° C. => >5 min. |
| | | 45° C. => >5 min. |
| | 3. Tackiness | Very Tacky |
| | Batch No. SG/002 Formulation: | |
| Part A: | Distilled water | 83.50 g |
| | Carbopol | 00.62 g |
| | TEA | 01.20 g |
| Part B: | Distilled water | 1.0 g |
| | Propylene glycol | 5.0 g |
| | TEA | 1.5 gm |

Procedure: Weigh the given amount of Distilled water from part A and keep in water bath at 70° C. Add Carbopol to Distilled water with constant stirring to avoid lumps. Add TEA to it at 70° C. after 20 minutes. Weigh all the ingredients from part B and keep in water bath at 70° C. for 15-20 min. Add part B to part A and stir it for 10-15 min. Cool it to room temperature and analyze.

| Results | 1. pH 7.9 (SOP-08) | |
|---|---|---|
| | 2. Flow-ability | 90° C. => >5 min |
| | | 45° C. => >5 min |
| | 3. Tackiness | Very Tacky |
| | Batch No. SG/003 Formulation: | |
| Part A: | Distilled water | 86.00 g |
| | Carbopol | 00.62 g |
| | TEA | 01.20 g |
| Part B: | Distilled water | 2.00 g |
| | Propylene glycol | 5.00 g |
| | TEA | 1.50 g |

Procedure: Weigh the given amount of Distilled water from part A and keep in water bath at 70° C. Add Carbopol to Distilled water with constant stirring to avoid lumps. Add TEA to it at 70° C. after 20 minutes. Weigh all the ingredients from part B and keep in water bath at 70° C. for 15-20 min. Add part B to part A and stir it for 10-15 min. Cool it to room temperature and analyze.

| Results | 1. pH | 8.62 |
|---|---|---|
| | 2. Flow-ability | 90° C. => >5 min. |
| | | 45° C. => >5 min |
| | 3. Tackiness | Very Tacky. |
| | Batch No. SG/004 Formulation: | |
| Part A: | Distilled water | 86.00 g |
| | Carbopol | 00.62 g |
| | TEA | 01.00 g |
| Part B: | Distilled water | 2.00 g |
| | Propylene glycol | 5.00 g |
| | TEA | 1.50 g |

Procedure: Weigh the given amount of Distilled water from Part A and keep in water bath at 70° C. Add Carbopol to Distilled Water with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results: | 1. pH | 8.5 |
|---|---|---|
| | 2. Flow-ability | 90° C. => >5 min. |
| | | 45° C. => >5 min. |
| | 3. Tackiness | Very Tacky |
| | Batch No. SG/005 Formulation: | |
| Part A: | Distilled water | 86.0 g |
| | Carbopol | 0.62 |
| | TEA | 1.20 g |
| Part B: | Distilled water | 2.00 g |
| | Propylene glycol | 7.00 g |
| | TEA | 1.50 g |

Procedure: Weigh the given amount of Distilled Water from Part A and keep in water bath at 70° C. Add Carbopol to Distilled Water with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 8.7 |
| --- | --- | --- |
| | 2. Flow-ability | 90° C. => >5 min. |
| | | 45° C. => >5 min. |
| | 3. Tackiness | Very Tacky |
| | Batch No. SG/006 Formulation: | |
| Part A: | Distilled water | 85.00 g |
| | Carbopol | 00.62 g |
| | TEA | 01.00 g |
| Part B: | Distilled water | 1.00 g |
| | Propylene glycol | 5.00 g |
| | TEA | 1.40 g |

Procedure: Weigh the given amount of Distilled Water from Part A and keep in water bath at 70° C. Add Carbopol to Distilled Water with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 8.4 |
| --- | --- | --- |
| | 2. Flow-ability | 90° C. => >5 min |
| | | 45° C. => >5 min |
| | 3. Tackiness | Very Tacky |
| | Batch No. SG/007 Formulation: | |
| Part A: | Distilled Water | 172 g |
| | Carbopol | 1.24 g |
| | TEA | 2.40 g |
| Part B: | Distilled Water | 6.0 g |
| | Propylene glycol | 10 g |
| | TEA | 2.80 g |

Procedure: Weigh the given amount of Distilled Water from Part A and keep in water bath at 70° C. Add Carbopol to Distilled Water with constant stirring to avoid lumps. Add TEA to it at 70° C. after 20 minutes. Weigh all the ingredients from Part B and keep in water bath at 70° C. for 15-20 min. Add Part B to part A and stir it for 10-15 min. Cool it to room temperature and analyze.

| Results | 1. pH | 8.28 |
| --- | --- | --- |
| | 2. Flow-ability | 90° C. => >5 min. |
| | | 45° C. => >5 min. |
| | 3. Tackiness | Very Tacky |
| | Batch No. SG/008 Formulation: | |
| Part A: | Silver Solution (32 ppm) | 86 g |
| | Carbopol | 0.62 g |
| | TEA | 1.20 g |
| Part B | Silver Solution (32 ppm) | 2.0 g |
| | Propylene glycol | 5.0 |
| | TEA | 1.5 g |

Procedure: Weigh the given amount of Silver Solution from part A and keep in water bath at 70° C. Add Carbopol to Silver Solution with constant stirring to avoid lumps. Add TEA to it at 70° C. after 20 minutes. Weigh all the ingredients from Part B and keep in water bath at 70° C. for 15-20 min. Add Part B to part A and stir it for 10-15 min. Cool it to room temperature and analyze.

| Results | 1. pH | 8.65 |
| --- | --- | --- |
| | 2. Flow-ability | 90° C. => >5 min. |
| | | 45° C. => >5 min. |
| | 3. Tackiness | Very Tacky |
| | Batch No. SG/009 Formulation: | |
| Part A: | Silver Solution (32 ppm) | 172 g |
| | Distilled Water | 12 g |
| | Carbopol | 1.24 g |
| | TEA | 2.40 g |
| Part B: | Silver Solution (32 ppm) | 6.00 g |
| | Propylene glycol | 10.0 g |
| | TEA | 2.80 g |

Procedure: Weigh the given amount of Silver Solution from part A and keep in water bath at 70° C. Add Carbopol to Silver Solution with constant stirring to avoid lumps. Add TEA to it at 70° C. after 20 minutes. Weigh all the ingredients from Part B and keep in water bath at 70° C. for 15-20 min. Add Part B to part A and stir it for 10-15 min. Cool it to room temperature and analyze.

| Results: | 1. pH | 8.54 |
| --- | --- | --- |
| | 2. Flow-ability: | 90° C. => >5 min. |
| | | 45° C. => >5 min. |
| | 3. Tackiness | Very Tacky |
| | Batch No. SGI010 Formulation: | |
| Part A: | Silver Solution (32 ppm) | 172 g |
| | Distilled Water | 24 g |
| | Carbopol | 1.39 g |
| | TEA | 2.40 g |
| Part B: | Silver Solution (32 ppm) | 6.00 g |
| | Propylene glycol | 5.00 g |
| | TEA | 2.80 g |

Procedure: Weigh the given amount of Silver Solution from part A and keep in water bath at 70° C. Add Carbopol to Silver Solution with constant stirring to avoid lumps. Add TEA to it at 70° C. after 20 minutes. Weigh all the ingredients from Part B and keep in water bath at 70° C. for 15-20 min. Add Part B to part A and stir it for 10-15 min. Cool it to room temperature and analyze.

| Results | 1. pH | 8.43 |
| --- | --- | --- |
| | 2. Flow-ability | 90° C. => >5 min. |
| | | 45° C. => >5 min. |
| | 3. Tackiness | Tacky |
| | Batch No. SG/011 Formulation: | |
| Part A: | Distilled Water | 98 g |
| | Carbopol | 0.76 g |
| | TEA | 0.56 g |
| Part B: | Distilled Water | 3.0 g |
| | Propylene glycol | 5.0 g |
| | TEA | 1.4 g |

Procedure: Weigh the given amount of Distilled Water from Part A and keep in water bath at 70° C. Add Carbopol to Distilled Water Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results: | 1. pH | 8.05 |
|---|---|---|
| | 2. Flow-ability | 90° C. => >5 min. |
| | | 45° C. => >5 min. |
| | 3. Tackiness | Very Tacky |
| | Batch No. SG1012 Formulation: | |
| Part A | Distilled water | 98 g |
| | Carbopol | 0.76 g |
| | TEA | 0.34 g |
| Part B | Distilled Water | 3.00 g |
| | Propylene glycol | 5.00 g |
| | TEA | 0.64 g |

Procedure: Weigh the given amount of Distilled Water from Part A and keep in water bath at 70° C. Add Carbopol to Distilled Water Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 6.35 |
|---|---|---|
| | 2. Flow-ability | 90° C. => >5 min. |
| | | 45° C. => >5 min. |
| | 3. Tackiness | Very Tacky |
| | Batch No. SG/013 Formulation: | |
| Part A: | Silver Solution (32 ppm) | 86 g |
| | Distilled Water | 12 g |
| | Carbopol | 0.76 g |
| | TEA | 0.32 g |
| Part B: | Silver Solution (32 ppm) | 3.00 g |
| | Propylene glycol | 5.00 g |
| | TEA | 0.64 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results: | 1. pH | 6.7 |
|---|---|---|
| | 2. Flow-ability | 90° C. => >5 min. |
| | | 45° C. => >5 min. |
| | 3. Tackiness | Very Tacky |
| | Batch No. SG/014 Formulation: | |
| Part A: | Silver Solution (32 ppm) | 86 g |
| | Distilled Water | 12 g |
| | Carbopol | 0.78 g |
| | TEA | 0.32 gm |
| Part B | Silver Solution (32 ppm): | 3.00 g |
| | Propylene glycol | 5.00 g |
| | TEA | 0.64 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 6.6 |
|---|---|---|
| | 2. Flow-ability | 90° C. => >5 min. |
| | | 45° C. => >5 min. |
| | 3. Tackiness | Very Tacky |
| | Batch No. SG/015 Formulation: | |
| Part A | Silver Solution (32 ppm) | 86 g |
| | Distilled Water | 12 g |
| | Carbopol | 0.68 g |
| | TEA | 0.40 g |
| Part B | Silver Solution (32 ppm): | 5.0 g |
| | Propylene glycol | 7.0 g |
| | TEA | 0.6 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 6.72 |
|---|---|---|
| | 2. Flow-ability | 90° C. => >5 min. |
| | | 45° C. => >5 min |
| | 3. Tackiness | Tacky |
| | Batch No. SG/016 Formulation: | |
| Part A: | Silver Solution (32 ppm) | 86 g |
| | Distilled Water | 12 g |
| | Carbopol | 0.64 g |
| | TEA | 0.40 g |
| Part B: | Silver Solution (32 ppm) | 5.0 g |
| | Propylene glycol | 7.0 g |
| | TEA | 0.6 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 mins. Weigh all the ingredients from Part B and keep in water bath at 70° C. for 15-20 min. Add Part B to Part A and stir it for 10-15 min. Cool it to room temperature and analyze.

| Results: | 1. pH | 6.87 |
|---|---|---|
| | 2. Flow-ability | 90° C. => >5 min. |
| | | 45° C. => >5 min |
| | 3. Tackiness | Tacky |
| | Batch No. SG/017 Formulation: | |
| Part A: | Silver Solution (32 ppm) | 86 g |
| | Distilled Water | 12 g |
| | Carbopol | 0.62 g |
| | TEA | 0.4 g |
| Part B: | Silver Solution (32 ppm) | 5.0 g |
| | Propylene glycol | 7.0 g |
| | TEA | 0.6 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results: | 1. pH | 7.05 |
| --- | --- | --- |
| | 2. Flow-ability | 90° C. => >5 min. |
| | | 45° C. => >5 min |
| | 3. Tackiness | Tacky |
| | Batch No. SG/018 Formulation: | |
| Part A: | Silver Solution (32 ppm) | 86 g |
| | Distilled Water | 12 g |
| | Carbopol | 0.58 g |
| | TEA | 0.4 g |
| Part B: | Silver Solution (32 ppm) | 5.0 g |
| | Propylene glycol | 7.0 g |
| | TEA | 0.6 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 7.40 |
| --- | --- | --- |
| | 2. Flow-ability | 90° C. => >5 min. |
| | | 45° C. => >5 min |
| | 3. Tackiness | Smooth |
| | Batch No. SG/019 Formulation: | |
| Part A: | Silver Solution (32 ppm) | 86 g |
| | Distilled water | 12 g |
| | Carbopol | 0.54 g |
| | TEA | 0.4 g |
| Part B: | Silver Solution (32 ppm) | 5.0 g |
| | Propylene glycol | 7.0 g |
| | TEA | 0.6 g |

Procedure: Weigh the given amount of Silver Solution & Distilled Water from Part A and keep in water bath at 70° C. Add Carbopol to Solution with constant stirring to avoid lumps. Add TEA to it at 70° C. after 20 minutes. Weigh all the ingredients from Part B and keep in water bath at 70° C. for 15-20 min. Add Part B to Part A and stir it for 10-15 min. Cool it to room temperature and analyze.

| Results | 1. pH | 7.65 |
| --- | --- | --- |
| | 2. Flow-ability | 90° C. => 1 min. |
| | | 45° C. => 2 min |
| | 3. Tackiness | Smooth |

Remark:
Though the Gel feel has improved consistency is not suitable.
Based on the above results the following instructions for a one kilogram batch were developed.

| Part B | Silver Solution | 860 gm |
| --- | --- | --- |
| | Distilled water | 100 gm |
| | Carbopol | 5.80 gm |
| | TEA | 4.00 gm |
| | ASAP Solution | 50.0 gm |
| | Propylene glycol | 70.0 gm |
| | TEA | 6.00 gm |

Yield 1.0 Kg. after adjusting for moisture loss.

Procedure: in a clean sterilized vessel take the required quantity of Distilled Water & silver solution. Raise the temperature of solution to 70° C. with continuous stirring. Start addition of Carbopol in minute amounts with continuous stirring/homogenization. After all Carbopol has been added continue for 30 minutes. (Adjust time according to batch size). Then add TEA into the phase A solution.

In a separate vessel mix all ingredients of part B. Raise the temperature to 70° C. & slowly add part B to Part A. On complete homogenization cool it to room temperature.

Precautions:
Carbopol dispersion must be done using a good homogenizer.
Take a small trial batch when using a new lot of Carbopol.
Minimize Heating time as longer heating leads to more water loss.

| Results | 1. pH | 7.4 |
| --- | --- | --- |
| | 2. Flow-ability | >5 min. |
| | 3. Tackiness | Smooth. |

This formulation has been readily scaled up to 10 kgs. in a pilot plant. No problems were encountered during scale up. Deaeration by vacuum application is recommended to remove entrapped air and ensure uniform filling.

This formulation has the following physical and chemical characteristics.

| | TEST | SPECIFICATION | RESULTS |
| --- | --- | --- | --- |
| 1. | Appearance | Golden yellow Translucent Gel | Passes |
| 2. | Odor | Odorless | Odorless |
| 3. | Specific Gravity | 1.02 | 1.02 |
| 4. | Flowability | At 45° & 90° - More than 5 min. to travel 1 inch from the origin | At 45° & 90° - More than 5 min. to travel 1 inch from the origin |
| 5. | Foaming Cap. | <10 ml | <10 ml |
| 6. | Feel/Tackiness | 1-Smooth | 1-Smooth |
| 7 | Viscosity RT 30° 370 | 32,000 ± 5000 30,000 + 5000 | 34,000 33,500 |
| 8. | PH | 6.5 to 8.0 | 7.4 |
| 9. | Freeze & Thaw | To pass SOP 1–10 | Compares with Original |
| 10. | Optimum Wavelength (X Max) | 22 ppm - 400 +/- 20 nm. 32 ppm - 450 +/- 20 nm. | 400 nm. ** 450 nm. ** |
| 11. | Light Exposure | No further discoloration | Passes. |
| 12. | Compatibility | No discoloration of product I reaction with containers. | Ref Table 3 |
| 13. | Moisture Donation | — | 10.27% |
| 14. | Moisture Uptake | — | 80% |

Microbiological Evaluation

It is reasonable to assume that the silver colloid hydrogel has microbiological proprieties similar to the original silver colloid which has been extensively tested as demonstrated above. However, the addition of the hydrophilic polymer to produce the gel might directly interfere with the microbial properties of the silver or might so inhibit diffusion of the silver that effectiveness is decreased. Therefore, microbiological tests similar to those carried out on the silver colloid solution were also performed on the silver colloid hydrogel.

Initially, the hydrogel was tested to determine whether the composition was self-sterilizing. The following protocol was followed:

Flasks of 100 ml sterile Fluid Thioglycollate Medium (Anaerobic bacteria), sterile Soya bean Casein Digest Medium (Aerobic bacteria), and Potato Dextrose Broth (Fungi) were obtained Samples of about 100 mg of gel to be tested were aseptically transferred into sets of flask. One set was incubated at 37° C. and another set was incubated at room temperature for one week. After that time the flasks were inspected and showed no turbidity or sign of microbial growth. Because the gel sample had not been manufactured under sterile conditions, it can be concluded that the composition is self-sterilizing. The 100 mg of gel used for each test This corresponds to 2.2 µg in 100 ml medium or 0.02214 or 0.032 µg of silver per ml of medium. At this concentration silver would not have antimicrobial activity and hence false negative results can be eliminated.

A variety of test organisms were then used to compare the zone of inhibition attained with either 22 or 32 ppm silver solution or 22 or 32 ppm silver gel made as described above. Aliquots of 0.1 ml or actively growing 18 hr cultures of each microorganism (approximately $10^8$ CFU/ml) were spread on sterile nutrient agar plates. A 10 mm diameter hole was punched in each inoculated plate with a cork borer. a test amount of (0/2-0.3 g) of the product was placed into each hole, and the plate was incubated for 24 hr. After that time the plates were inspected and the following zones of inhibition (total diameter of each zone) were measured.

|  | Silver Solution | | Silver Gel | |
|---|---|---|---|---|
| Culture | 22 ppm | 32 ppm | 22 ppm | 32 ppm |
| E. coil | 14 mm | 14 mm | 12 mm | 13 mm |
| Ps. Aeruginosa | 21 mm | 22 mm | 21 mm | 20 mm |
| B. subtilis | 15 mm | 16 mm | 14 mm | 14 mm |
| MRSA 1 | 17 mm | 18 mm | 16 mm | 17 mm |
| MRSA 2 | 16 mm | 17 mm | 16 mm | 17 mm |
| S. aureus ATCC 6538 P | 14 mm | 14.5 mm | 15 mm | 15 mm |
| S. pyogenes | 16 mm | 18 mm | 16 mm | 18 mm |
| S. typhi | 17 mm | 16 mm | 16 mm | 16 mm |
| Sh. flexneri | 20 mm | 21 mm | 20 mm | 21 mm |
| K. pneumoniae | 17 mm | 18 mm | 18 mm | 18 mm |
| C. diptheriae | 16 mm | 18 mm | 16 mm | 17 mm |
| C. albicans | 39 mm | 40 mm | 39 mm | 40 mm |

These results show that the inhibitory effects of the gel are essentially equivalent to those of the silver colloid solution; this demonstrates that the gelling polymer does not negatively affect the antimicrobial powers of the silver colloid. Some cultures (*S. pyogenes, C. diphtheriae* and *S. aureus*) were also cultured on Blood Agar. The results suggested that the silver gel would also be effective on a bloody, exuding wounds.

Similar tests were carried out on the same bacterial strains using a variety of antibiotic agents. In some cases the antibiotics were more effective than the silver compounds—in others they were much less effective. This demonstrates that the strains used were not weakened or "push-over" strains.

Gram Positive Bacteria

| Antibiotic | Conc. | S. aureus | MRSA 1 | MRSA 2 | B. subtilis |
|---|---|---|---|---|---|
| Ampicillin | 200 mcg | Clear | 15 mm | 18 mm | 16 mm |
| Cefotaxime | 30 mcg | 26 mm | No inhibition | -Clear | 12 mm |
| Cephalexin | 30 mcg | Clear | 1.0 mm | 0.8 mm | Clear |
| Ciprofloxacin | 5 mcg | 28 mm | 14 mm | 14 mm | 20 mm |
| Cloxacillin | 1 mcg | Clear | Clear | 13 mm | 18 mm |
| Co-Trimoxazole | 25 mcg | Clear | No inhibition | No inhibition | 15 mm |
| Gentamycin | 10 mcg | Clear | No inhibition | 11 mm | 18 mm |
| Lincomycin | 2 mcg | Clear | Clear | Clear | 18 mm |
| Ofloxacin | 5 mcg | Clear | 15 mm | 16 mm | 22 mm |
| Pefloxacin | 10 mcg | 30 mm | 11 mm | 13 mm | 21 mm |
| Roxythromycin | 15 mcg | Clear | 1.0 mm | 12 mm | 20 mm |
| Tetracyclin | 30 mcg | 34 mm | No inhibition | 0.7 mm | 19 mm |

Gram Negative Bacteria

| Antibiotics | Conc. | E. coli | K. pneumoniae | S. typhi | Ps. aeruginosa |
|---|---|---|---|---|---|
| Amikacin | 30 mcg | Clear | 18 mm | Clear | 10 mm |
| Ampicillin | 200 mcg | 23 mm | 18 mm | 20 mm | 13 mm |
| Cefotaxime | 30 mcg | 21 mm | 20 mm | 22 mm | 19 mm |
| Ceftizoxime | 30 mcg | 18 mm | 18 mm | 15 mm | No inhibition |
| Chloramphenicol | 30 mcg | 22 mm | 21 mm | 23 mm | No inhibition |
| Ciprofloxacin | 5 mcg | 29 mm | 22 mm | 25 mm | 15 mm |
| Co-Trimoxazole | 25 mcg | 24 mm | 19 mm | 27 mm | Clear |
| Gentamycin | 10 mcg | Clear | 17 mm | Clear | No inhibition |
| Ofloxacin | 5 mcg | Clear- | 29 mm | clear | 15 mm |
| Pefloxacin | 10 mcg | Clear | 25 mm | clear | 10 mm |
| Piperacillin | 100 mcg | 22 mm | 15 mm | 16 mm | 10 mm |
| Tetracyclin | 30 mcg | 19 mm | 18 mm | 16 mm | No inhibition |

Hand Scrub Test

Since the hydrogel has the ability to increase the adherence of silver to skin surfaces, effectiveness of the gel as a hand scrub was evaluated. For this test a one inch square of a volunteers hand was marked and then scrubbed with about 1 g of the gel. A control area was scrubbed with sterile distilled water. The areas were swabbed and the swab streaked on nutrient agar. The swabbing was repeated every hour for four hours. The streaked plates were incubated for 24 hr at 37° C. and the results evaluated.

As shown in the following table, the control swabs grew so many bacteria as to be Too Numerous To Count (TNTC). The areas treated with silver gel remained essentially sterile for three hours and showed only slight growth at four hours. This should provide superior results for health care workers who need to sterilize the surface of their hands without using harsh or irrigating compounds.

| Time | Control | 22 ppm | 32 ppm |
|---|---|---|---|
| 0 hr | TNTC | No growth | No growth |
| 1 hr | TNTC | No growth | No growth |
| 2 hr | TNTC | No growth | No growth |
| 3 hr | TNTC | No growth | No growth |
| 4 hr | TNTC | 3 Cfu | 2 Cfu |

Although hydrogels show exceptional wound healing properties, a drawback of the typical hydrogel is that microorganisms are often able to migrate through the matrix. Thus, if a would is covered by hydrogel and one area of the wound becomes infected, the infectious organisms may be able to travel through the hydrogel an infect other regions. This possibility was tested by using a strip of hydrogel to bridge separated regions on a nutrient agar plate. Each agar plate was separated into two regions by removing a 2 cm strip of agar along a diameter of the plate. This gap was bridged by a 1.5 cm wide strip of hydrogel that overlapped onto the agar by about 5 mm at either end. One side of the plate was then inoculated with about 0.5 ml of culture and the plate was incubated to see if the microorganisms could cross the hydrogel "bridge." The results show that silver hydrogel completely prevented migration.

| Culture | Zone of Inoculation | Zone of Migration |
|---|---|---|
| E. coil | Heavy Growth | No Growth |
| B. subtilis | Heavy Growth | No Growth |
| MRSA 1 | Heavy Growth | No Growth |
| Ps. aeruginosa | Heavy Growth | No Growth |
| Hydrogel control | Heavy Growth | Growth |

From the results shown above a prototype gel formula was selected and the variations are suggested in the following examples.

Example 1

For a 1 Kg batch of gel take components of Part A and Part B as given below:

| Part A | Inventive silver colloid 32 ppm | 860 g |
|---|---|---|
| | Distilled Water | 100 g |
| | Carbapol | 6.8 g |
| | Triethanolamine | 4.0 g |
| Part B | nventive silver colloid 32 ppm | 50 g |
| | Propylene Glycol | 70 g |
| | Triethanolamine | 6.0 g |

First take required amount of distilled water and silver solution in a stirrer and start stirring. Slowly add in Carbapol (Noveon, USA). Stirring should be sufficiently vigorous to dispense the Carbapol and avoid formation of lumps. Temperature should be maintained between 60-70° C. during stirring.

Mix all ingredients of Part B in a beaker. Heat to 70° C. and add to Part A under vigorous stirring. Continue mixing and cool to room temperature. Check yield of batch. It should be approx. 1000 gm. The triethanolamine causes the Carbopol to gel.

Example 2

Prepare all ingredients as in Example 1 including the addition of 1% collagen. This will give a gel with both antimicrobial as well as benefits of collagen which has scaffolding type of wound healing acceleration.

Example 3

Prepare all ingredients as in Example 1 but including the addition of Aloe vera (powder or solution) in the range of 1-5%. This will confer additional wound healing properties.

Example 4

Prepare all ingredients as in Example 1 with the addition of 1-10% by weight Maltodextrin. This will provide a gel formulation which stimulates wound granulation.

Summary of Silver Hydrogel Results

It was possible to prepare Carbopol based gels using inventive silver colloid solutions of 22 ppm & 32 ppm. The gel thus prepared have many advantage over their solution counterparts by virtue of their capacity to remain in place while retaining the properties of the parent silver solutions. The amorphous hydrogel nature of the medicament confers the advantage of moist wound healing acceleration and also limiting the severity of burns wound by limiting the thermal shock. Moreover, the active agent, colloidal silver solution has been tested on a cell line in an earlier study and found to be non-cytotoxic.

A thorough physico-chemical evaluation of the gel has been done with various batches and series of series of detailed methods were prepared to standardize and control product and processes during manufacture.

Microbiological studies were carried out in depth and show that the gel retains its bactericidal nature. Silver migration studies have been simulated and conclusively demonstrate that the gel can deliver silver over a period of time to the wound. The formulation design will also not allow microbe migration inside from outside and vice versa.

These tests demonstrate that hypothetical evaluation of the silver hydrogel on the basis of a publication (Journal of Wound Care Vol 12, No 8 SEPT 2003) where alternative silver based dressings were evaluated with points given for:
1. Antimicrobial zone of inhibition;
2. Microbial challenge test;
3. Microbial transmission test; and
4. Silver content of dressings.

In the first test the silver hydrogel would be placed in group B and in all three remaining tests the silver hydrogel would score in group A giving it a total points of 20, on par with Calgitrol Ag & Acticot, commercial products which scored the highest in this evaluation.

The antibacterial and antiviral properties of the colloidal silver solution open up several significant uses for the silver hydrogel beyond a wound dressing. As demonstrated above the hydrogel is an ideal antibacterial hand scrub. In addition, the nonirritating character of the silver colloid and the hydrogel make the combination an ideal personal lubricant for male or female sexual use with or without condoms or diaphragms where the combination would combat bacteria, fungi (note the effectiveness on *Candida albicans*) and dangerous virus such as HIV and disinfect reusable barriers such as diaphragms. Since the hydrogel contains little if any oil, it has no harmful effects on condoms or diaphragms, unlike certain other personal lubricants.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. A hydrogel composition comprising a hydrophilic acrylic acid copolymers dissolved in a composition of silver in water having a total concentration of silver of between about 5 and 40 parts per million, wherein said silver is in the form of a stable and colorless colloidal suspension of silver particles having an interior of metallic silver and an exterior surface of ionic silver oxide, wherein at least 75% of the silver particles have diameters between 0.005 micrometers and 0.015 micrometers, wherein said silver particles are made from a silver electrode in an electrochemical cell, and wherein the composition manifests antimicrobial properties.

2. The composition according to claim 1, wherein at least 90% of the colloidal silver particles have diameters between 0.005 micrometers and 0.015 micrometers.

3. The composition according to claim 2, wherein at least 95% of the colloidal silver particles have diameters between 0.005 micrometers and 0.015 micrometers.

4. The composition according to claim 1 further comprising hydrogen peroxide.

5. The composition according to claim 4, wherein the hydrogen peroxide concentration is between about 1% weight/vol and about 3.0% weight/vol.

6. The composition according to claim 1, wherein the composition manifests antimicrobial properties against microbes selected from the group consisting of *Bacillus anthracis, Bacillus subtilis, Candida albicans, Mycobacteria bovis, Mycobacteria tuberculosis, Pseudomonas aeruginosa, Salmonella choleraesius, Staphylococcus aureus, Trichomonas vaginalis,* and *Yersinia pestis*.

7. The composition according to claim 6, wherein *Staphylococcus aureus* is a methicillin-resistant strain.

8. The composition according to claim 1, wherein the composition manifests antimicrobial properties against microbes associated with diseases selected from the group consisting of malaria, fungal infections of the skin, bacterial infections of the skin, vaginal infections, urinary tract infections, tonsillitis, pelvic inflammatory disease, pharyngitis, gonorrhea, conjunctivitis, otitis, respiratory tract infections, and nasal infections.

9. The composition according to claim 1, further comprising additives to enhance physical characteristics of the hydrogel and/or enhance wound healing.

10. The composition according to claim 9, wherein the additives are selected from the group consisting of vitamins, amino acids, growth factors, maltodextrin, aloe vera and anesthetics.

11. The composition according to claim 1, further comprising additional antimicrobial agents.

12. The composition according to claim 11, wherein the additional antimicrobial agents are selected from the group consisting of organic acids, alcohols, organic disinfectants, chlorinated phenolics, chlorhexidine, biguanides, surfactants, aldehydes, halogen disinfectants and oxygenating disinfectants.

* * * * *